United States Patent
Heyduk

(12) 
(10) Patent No.: US 6,544,746 B2
(45) Date of Patent: Apr. 8, 2003

(54) RAPID AND SENSITIVE PROXIMITY-BASED ASSAY FOR THE DETECTION AND QUANTIFICATION OF DNA BINDING PROTEINS

(75) Inventor: Tomasz Heyduk, Ballwin, MO (US)

(73) Assignee: St. Louis University, St. Louis, MO (US)

( * ) Notice: Subject to any disclaimer, the term of this patent is extended or adjusted under 35 U.S.C. 154(b) by 0 days.

(21) Appl. No.: 09/928,385

(22) Filed: Aug. 13, 2001

(65) Prior Publication Data

US 2003/0049625 A1 Mar. 13, 2003

(51) Int. Cl.⁷ .............................. C12Q 1/68; C12Q 1/34; C12P 19/34; C07H 21/04; C07H 21/02
(52) U.S. Cl. .............................. 435/6; 435/18; 435/91.2; 536/24.3; 536/24.31; 536/24.32; 536/24.33; 536/23.1
(58) Field of Search .............................. 435/6, 18, 91.2; 536/24.3, 24.31, 24.32, 24.33, 23.1

(56) References Cited

U.S. PATENT DOCUMENTS

| | | | | |
|---|---|---|---|---|
| 5,763,181 | A | * | 6/1998 | Han et al. |
| 6,171,779 | B1 | * | 1/2001 | Chada et al. |
| 6,355,428 | B1 | * | 3/2001 | Schroth et al. |
| 6,210,896 | B1 | * | 4/2001 | Chan |
| 6,248,532 | B1 | * | 6/2001 | Keegan |
| 6,265,213 | B1 | * | 7/2001 | Morgan et al. |
| 6,297,059 | B1 | * | 10/2001 | Song et al. |
| 6,358,679 | B1 | * | 3/2002 | Heid et al. |

FOREIGN PATENT DOCUMENTS

WO  WO00/40753  7/2000

OTHER PUBLICATIONS

Bailey et al., Biochemistry, vol. 34, *Interaction between the Escherichia coli Regulatory Protein TyrR and DNA: A Fluorescence Footprinting Study*; pp. 15802–15812, 1995.
Bjornson et al., Biochemistry, vol. 35, *Kinetic Mechanism of DNA Binding and DNA–Induced Dimerization of the Escherichia coli Rep Helicase*, pp. 2268–2282, 1996.
Campbell et al., Chem. J., vol. 216, *A homogeneous immunoassay of cyclic nucleotides based on chemiluminescence energy transfer*, pp. 185–194, 1983.
Fried et al., Nucleic Acids Research, vol. 9, No. 23, *Equilibria and kinetics of lac repressor–operator interactions by polyacrylamide gel electrophoresis*, pp. 6505–6525, 1981.
Galas et al., Nucleic Acids Research, vol. 5, No. 9, *DNAase footprinting: a simple method for the detection of protein–DNA biding specificity*, pp. 3157–3170, Sep., 1978.
Gourves et al., Journal of Biol. Chem., vol. 275, No. 15, *Equilibrium Binding of Single–stranded DNA with Herpes Simplex Virus Type I–coded Single–stranded DNA–binding Protein, ICP8*, pp. 10864–10869, Apr. 14, 2000.

Hey et al., Biochemistry, vol. 40, *Binding of XPA and RPA to Damaged DNA Investigated by Fluorescence Anisotropy*, pp. 2901–2910, 2001.
Heyduk et al., Analytical Biochemistry, vol. 248, *Thiol–Reactive, Luminescent Europium Chelates: Luminescence Probes for Resonance Energy Transfer Distance Measurements of Biomolecules*, pp. 216–227, 1997.
Heyduk et al., Proc. Natl. Acad. Sci. USA, vol. 87, *Application of fluorescence energy transfer and polarization to monitor Escherichia coli cAMP receptor protein and lac promoter interaction*, pp. 1744–1748, Mar. 1990.
Hill et al., Methods in Enzymology, vol. 278, *Fluorescence Approaches to Study of Protein–Nucleic Acid Complexation*, pp. 390–416, 1997.
Lima et al., PNAS, vol. 97, No. 26, *DNA tightens the dimeric DNA–binding domain of human papillomavirus E2 protein without changes in volume*, p. 14298–14294, Dec. 19, 2000.
Maiti et al., Proc. Natl. Acad. Sci. USA, vol. 94, *Fluorescence correlation spectroscopy: Diagnostics for sparse molecules*, pp. 11753–11757, Oct. 1997.
Mathis, Clin. Chem., vol. 41, No. 9, *Probing Molecular Interactions with Homogeneous Techniques Based on Rare Earth Cryptates and Fluorescence Entergy Transfer*, pp. 1391–1397, 1995.
Ozers et al., J. of Biol. Chem., vol. 272, No. 48, *Equilibrium Binding of Estrogen Receptor with DNA Using Fluorescence Anistropy*, pp. 30405–30411, Nov. 28, 1997.
Parkhurst et al., Biochemistry, vol. 35, *Simultaneous Binding and Bending of Promoter DNA by the TATA Binding Protein: Real Time Kinetic Measurements*, pp. 7459–7465, 1996.
Reedstrom et al., J. Mol. Biol., vol. 273, *Affinity and Specificity of trp Repressor–DNA Interactions Studied with Fluorescent Oligonucleotides*, pp. 572–585, 1997.
Sha et al., J. of Biol. Chem., vol. 270, No. 33, *Anti–cooperative Biphasic Equilibrium Binding of Transcription Factor Upstream Stimulatory Factor to Its Cognate DNA Monitored by Protein Fluorescence Changes*, pp. 19325–19329, Aug. 18, 1995.

(List continued on next page.)

*Primary Examiner*—W. Gary Jones
*Assistant Examiner*—Arun Kr. Chakrabarti
(74) *Attorney, Agent, or Firm*—Thompson Coburn LLP

(57) ABSTRACT

Methods to determine the activity of any and all DNA binding factors, proteins or fragments thereof based upon the detection of a change in a luminescence or fluorescence signal are provided. Preferably, a fluorescence donor is attached to a nucleic acid comprising one portion of a DNA binding element and a fluorescence acceptor is attached to a nucleic acid comprising the other portion of the same binding element. Alternatively, a microsphere bead is attached to a nucleic acid comprising one portion of a binding element and a luminescent moiety or fluorochrome is attached to a nucleic acid comprising the other portion of the same binding element. Binding of a DNA binding factor to the nucleic acid components affects a change in luminescence. These methods may also be used to detect mediating analytes, to diagnose diseases and/or screen for drugs that mediate the activity of DNA binding factors.

46 Claims, 19 Drawing Sheets

OTHER PUBLICATIONS

Stryer, Ann. Rev. Biochem., vol. 47, *Fluorescence Energy Transfer as a Spectroscopic Ruler*, pp. 819–846, 1978.

Tyagi et al., Nature Biotechnology, vol. 16, *Multicolor molecular beacons for allele discrimination*, pp. 49–53, Jan. 1998.

Wang et al., Biochemistry, vol. 37, *Fluorescence Study of the Multiple Binding Equilibria of the Galactose Repressor*, pp. 41–50, 1998.

Weiss, Science, vol. 283, *Fluorescence Spectroscopy of Single Biomolecules*, pp. 1676–1683, Mar. 12, 1999.

Xu, Proc. Natl. Sci. USA, vol. 96, *A bioluminescence resonance energy transfer (BRET) system: Application to interacting circadian clock proteins*, pp. 151–156, Jan. 1999.

* cited by examiner

SEQUENCE LISTING

<160> NUMBER OF SEQ ID NOS: 24

<210> SEQ ID NO 1
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 1
aacgcaataa atgtga                                                    16

<210> SEQ ID NO 2
<211> LENGTH: 22
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 3
<223> OTHER INFORMATION: n = t labeled with fluorescein

<400> SEQUENCE: 2
agnagatcac attttaggca cc                                             22

<210> SEQ ID NO 3
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 3
ggtgcctaaa atgtga                                                    16

<210> SEQ ID NO 4
<211> LENGTH: 22
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 3
<223> OTHER INFORMATION: n = t labeled with dabcyl

<400> SEQUENCE: 4
tcnacttcac atttattgcg tt                                             22

<210> SEQ ID NO 5
<211> LENGTH: 30
<212> TYPE: DNA
<213> ORGANISM: artificial sequence
<220> FEATURE:
<221> NAME/KEY:
<222> LOCATION:
<223> OTHER INFORMATION: These sequences were chemically synthesized, but may also be created via recombinant methods.

<400> SEQUENCE: 5
cctaaaatgt gatctagatc acatttattg					30

<210> SEQ ID NO 6
<211> LENGTH: 30
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 6
gcatcggtca ctgcagtctc gacagctacg					30

<210> SEQ ID NO 7
<211> LENGTH: 22
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 3
<223> OTHER INFORMATION: n = amino modified thymine

<400> SEQUENCE: 7
agnagatcac attttaggca cc					22

<210> SEQ ID NO 8
<211> LENGTH: 22
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 3
<223> OTHER INFORMATION: n = amino modified thymine

<400> SEQUENCE: 8
tcnacttcac atttattgcg tt					22

<210> SEQ ID NO 9
<211> LENGTH: 38
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 2
<223> OTHER INFORMATION: n = fluorescein labeled thymine
<221> NAME/KEY: misc_feature
<222> LOCATION: 21...22
<223> OTHER INFORMATION: a non-nucleotide spacer element,
      18-O-Dimethoxytritylhexaethyleneglycol,1-[(2-cyanoethyl)-
      (N,N-diisopropyl)]-pho between nucleotides 21 and 22

<400> SEQUENCE: 9
cnagatcaca ttttaggcac caacgcaata aatgtgat					38

<210> SEQ ID NO 10
<211> LENGTH: 21
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 2
<223> OTHER INFORMATION: n = dabcyl labeled thymine

<400> SEQUENCE: 10
cnagatcaca tttattgcgt t                                          21

<210> SEQ ID NO 11
<211> LENGTH: 17
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 11
ggtgcctaaa atgtgat                                               17

<210> SEQ ID NO 12
<211> LENGTH: 17
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 12
ggtgtgtgga attgtga                                               17

<210> SEQ ID NO 13
<211> LENGTH: 22
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 4
<223> OTHER INFORMATION: n = fluorescein labeled thymine

<400> SEQUENCE: 13
gcgnataaca atttcacaca gg                                         22

<210> SEQ ID NO 14
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 14
cttgtgtgaa attgtt                                              16

```
<210> SEQ ID NO 15
<211> LENGTH: 23
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 2
<223> OTHER INFORMATION: n = dabcyl labeled thymine

<400> SEQUENCE: 15
```
anacgctcac aattccacac acc                                      23

```
<210> SEQ ID NO 16
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 16
```
gagatctatc gaacta                                              16

```
<210> SEQ ID NO 17
<211> LENGTH: 22
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 2
<223> OTHER INFORMATION: n = fluorescein labeled thymine

<400> SEQUENCE: 17
```
gnaaactagt acgaaactag ag                                       22

```
<210> SEQ ID NO 18
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 18
```
ctctagtttc gtacta                                              16

```
<210> SEQ ID NO 19
<211> LENGTH: 22
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
```

```
<221> NAME/KEY: modified_base
<222> LOCATION: 2
<223> OTHER INFORMATION: n = dabcyl labeled thymine

<400> SEQUENCE: 19
gnttactagt tcgatagatc tc                                              22

<210> SEQ ID NO 20
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 20
gcatcggtca cagaca                                                     16

<210> SEQ ID NO 21
<211> LENGTH: 26
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 5
<223> OTHER INFORMATION: n = fluorescein labeled thymine

<400> SEQUENCE: 21
tgccnagaca tgccttgcag tctcga                                          26

<210> SEQ ID NO 22
<211> LENGTH: 16
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.

<400> SEQUENCE: 22
tcgagactgc aaggca                                                     16

<210> SEQ ID NO 23
<211> LENGTH: 26
<212> TYPE: DNA
<213> ORGANISM: artificial sequence
<220> FEATURE:
<221> NAME/KEY:
<222> LOCATION:
<223> OTHER INFORMATION: These sequences were chemically synthesized,
      but may also be created via recombinant methods.
<221> NAME/KEY: modified_base
<222> LOCATION: 5
<223> OTHER INFORMATION: n = dabcyl labeled thymine

<400> SEQUENCE: 23
tgtcnaggca tgtctgtgac cgatgc                                          26

<210> SEQ ID NO 24
<211> LENGTH: 10
<212> TYPE: DNA
<213> ORGANISM: Homo sapiens
```

-continued

```
<220> FEATURE:
<221> NAME/KEY:
<222> LOCATION:
<223> OTHER INFORMATION: These sequences were chemically synthesized,
      but may also be created via recombinant methods.

<400> SEQUENCE: 24 rrrcwwgyyy                                                          10
```

US 6,544,746 B2

RAPID AND SENSITIVE PROXIMITY-BASED ASSAY FOR THE DETECTION AND QUANTIFICATION OF DNA BINDING PROTEINS

GOVERNMENTAL SUPPORT

This work was supported by the U.S. Department of Health and Human Services/National Institutes of Health grant number GM50514. The U.S. Government has certain rights in this invention.

SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f).

BACKGROUND OF THE INVENTION

1. Field of the Invention

The invention relates generally to methods of detecting and quantifying specific proteins, in particular sequence-specific DNA binding proteins, by changes in luminescence signal intensity or changes in color due to the processing of a calorimetric substrate. The invention is used in any application where the detection or quantification of DNA binding activity of a DNA binding protein is desired.

2. Description of the Related Art

The ability to detect and quantify specific protein molecules is of great importance in basic research and in clinical applications. Determination of the level of a specific protein is one of the most useful and important experimental procedures in biomedical research and molecular diagnostics. Cellular levels of specific proteins are commonly used as diagnostic markers for many diseases.

Protein-nucleic acid interactions are an extremely important and physiologically relevant type of macromolecular contact found in the cell. Many proteins that play an important role in regulating many cellular processes possess natural sequence-specific DNA binding activity. These proteins include transcription factors, chromatin remodeling factors and DNA maintenance enzymes. For a review of DNA binding proteins, see Benjamin Lewin, *Genes VII*, Oxford University Press, New York, 2000, which is herein incorporated by reference.

Transcription factors bind to specific cognate DNA elements, which include promoters, enhancers and silencer elements. They may be activators, repressors or both, depending on the cellular context, whose levels are important for regulation of gene expression. Thus, many of these proteins are important in disease development and disease diagnosis. For example, several transcription factors, which when overexpressed or inappropriately expressed, are oncogenes. These oncogenic transcription factors include myc, myb, fos, jun, rel and erb. Another cancer related transcription factor, p53, is involved in development of many cancers (Ko, L. L., and Prives, C. *Genes Dev.* 10, 1054–1072, 1996).

Chromatin remodeling factors are also important for the regulation of gene expression. Generally, regions of highly condensed chromatin, called heterochromatin, contain genes which are not actively transcribed, whereas regions of loose or non-condensed chromatin, called euchromatin, contain genes that are actively transcribed. During cellular differentiation, cancerous transformation and normal physiological homeostasis, chromatin may be remodeled. That is, some chromosomal regions become inaccessible to transcription factors and RNA polymerase, whereas other regions become accessible. Several DNA binding factors are involved in this dynamic process including nucleosome proteins (e.g., histones), histone acetyltransferases, histone deacetylases, DNA methyltransferases, nucleoplasmins, HMG proteins, repressor complex proteins, polycomb-related factors and trithorax-related factors.

DNA maintenance enzymes are DNA binding proteins necessary for the repair of damaged DNA, faithful replication of DNA and exchange of genetic information during recombination. Several types of cancer and other disease syndromes are the result of defective DNA maintenance enzymes. For example, Xeroderma pigmentosum, a horrific genetic disease whereby the sufferer is predisposed to skin cancer, is due to defective nucleotide-excision repair enzymes. Hereditary non-polyposis colorectal cancer is caused in large part by defective mismatch repair enzymes. Some forms of hereditary breast cancers are due to defective homologous recombination enzymes. For a review of genome maintenance systems and their role in cancer, see Hoeijmakers, J. H. J., Nature 411, 366–374, 2001, which is herein incorporated by reference. Thus, there is a significant interest in convenient and accurate methods for detecting, monitoring and/or quantifying DNA binding activity of DNA binding proteins.

The most common approaches taken to detect proteins exhibiting sequence-specific DNA binding activity are gel shift assays and various DNA footprinting assays (Fried, M.G., and Crothers, D. M. *Nucleic Acids Res.* 9, 6505–6525, 1981; Galas, D. J., and Schmitz, A. *Nucleic Acid Res.* 5, 3157–3170, 1978). These methods are laborious and time-consuming procedures, which typically involve the use of dangerous and expensive radioisotopes. Furthermore, these methods are not generally adaptable to high-throughput assay formats. Different fluorescence based methodologies for detecting and studying DNA binding proteins have been developed to overcome the deficiencies of gel shift and DNA footprinting assays.

Detection of molecules by fluorescence has several important advantages compared to alternative detection methods. Fluorescence provides an unmatched sensitivity of detection, as demonstrated by the detection of single molecules using fluorescence (Weiss, S. *Science* 283, 1676–1683, 1999). Detection of fluorescence, changes in fluorescence intensity or changes in emission spectra can be easily achieved by the selection of specific wavelengths of excitation and emission. Fluorescence provides a real-time signal allowing real-time monitoring of processes and real-time cellular imaging by microscopy (see Lakowicz, J. R. *Principles of Fluorescence Spectroscopy*, Kluwer Academic/Plenum Press, New York, 1999, which is herein incorporated by reference). Additionally, well-established methods and instrumentation for high-throughput detection of fluorescence signals exist in the art.

Current methods for detecting DNA binding proteins in solution using fluorescence rely on one of the following phenomena: (i) a change in the fluorescence intensity of a fluorochrome (also called a fluorophore or a fluorescent probe or label), which is present either on the protein or on the DNA, as a result of the perturbation of the microenvironment of the probe upon protein-DNA complex formation; (ii) a change of fluorescence polarization of the fluorochrome, which is present either on the protein or on the DNA, as a result of an increase in the molecular size of the protein-DNA complex relative to the unbound DNA or protein molecules; and (iii) resonance energy transfer between one fluorochrome present in DNA and another fluorochrome present in a protein as a result the proximity between DNA and the protein in protein-DNA complex. For a review on methods of detecting fluorescence signal detection, see Hill, J. J., and Royer, C. A. *Methods in Enzymol.* 278, 390–416, 1997, which is herein incorporated by reference.

In the first group of methods (group i), the change in the fluorescence signal is the result of a change in the microenvironment of the fluorescence probe which occurs upon the formation of a protein-DNA complex. Since the generation of the change in the fluorescence signal relies on the unpredictable chance that the formation of a protein-DNA complex will in fact change the environment of the fluorescence probe significantly enough to provide a measurable change in fluorescence, this approach is not generally applicable in that it will work in some cases but not in others. The outcome of such an assay depends on the nature of the protein, DNA sequence, the length of DNA fragment, identity of the fluorescence probe used, and the method of attachment of the fluorescence probe to DNA. Therefore, it is essentially impossible to predict when this method will or will not work since the mechanisms of the changes of fluorescence intensity due to the change in probe environment are not well understood. Examples of the application of this idea to the detection of protein-DNA complexes using fluorochromes attached to the protein or the DNA can be found in the following technical literature, which are herein incorporated by reference (Sha, M., Ferre-D'Amare, Burley, S. K., and Goss, D. J. *J. Biol. Chem.* 270, 19325–19329, 1995; Reedstrom, R. J., Brown, M. P., Grillo, A., Roen, D, and Royer, C. A. *J. Mol. Biol.* 273, 572–585, 1997; Erickson, G. H, and Daksis, J. WO 00/40753).

The unpredictability of such an assay format is illustrated in the literature. Some published studies demonstrate a significant change of fluorescence intensity upon protein-DNA complex formation. For example, a 50% quenching of fluorescein-labeled DNA was observed upon binding to the Trp repressor protein, and a similar degree of quenching was also observed upon glucocorticoid receptor binding to several different DNA targets (Reedstrom, R. J., Brown, M. P., Grillo, A., Roen, D, and Royer, C. A. *J. Mol. Biol.* 273, 572–20 585, 1997; Hill, J. J., and Royer, C. A. *Methods in Enzymol.* 278, 390–416, 1997). In other reports, either only small quenching or small increases of fluorescence emission have been observed (Bjornson, K. P., Moore, K. J. M., and Lohman, T. M. *Biochemistry* 35, 2268–2282, 1996; Hey, T., Lipps, G., and Krauss, G. *Biochemistry* 40, 2901–2910, 2001; Bailey, M., Hagmar, P., Millar, D. P., Davidson, B. E., Tong, G., Haralambidis, J., and Sawyer, W. H. *Biochemistry* 34, 15802–15812, 1995; Parkhurst, K. M., Brenowitz, M., and Parkhurst, L. J. *Biochemistry* 35, 7459–7465, 1996; Wang, K., Rodgers, M. E., Toptygin, D., Munsen, V. A., and Brand, L. *Biochemistry* 37, 41–50, 1998). Finally, in many reports no change of fluorescence intensity upon binding of the protein to the fluorochrome-labeled cognate nucleic acid was observed (Bailey, M., Hagmar, P., Millar, D. P., Davidson, B. E., Tong, G., Haralambidis, J., and Sawyer, W. H. Biochemistry 34, 15802–15812, 1995; Gourves, A. S., LeGac, N. T., Villani, G., Boehmer, P. E., and Johnson, N. P. *J. Biol. Chem.* 275, 10864–10869, 2000; Hey, T., Lipps, G., and Krauss, G. *Biochemistry* 40, 2901–2910, 2001; Lima, L. M. T. R., Foguel, D., and Silva, J. L. *Proc. Natl. Acad. Sci USA*, 97, 14289–14294, 2000; Ozers, M. S., Hill, J. J., Wood, E. K., Nardulli, A. M., Royer, C. A., and Gorski, J *J. Biol. Chem.* 272, 30405–30411, 1997; Reedstrom, R. J., Brown, M. P.,Grillo, A., Roen, D, and Royer, C. A. *J. Mol. Biol.* 273, 572–585, 1997; Wang, K., Rodgers, M. E.,Toptygin, D., Munsen, V. A., and Brand, L. *Biochemistry* 37, 41–50, 1998).

The lack of the predictability of the outcome of this assay format is perhaps best illustrated by the work described by Bailey et al. (supra), which examines the change in fluorescence of a DNA molecule labeled with fluorescein at eight different positions in response to binding of the TyrR protein. A change of fluorescence intensity was observed with only one specific DNA construct, whereas in the seven remaining cases no change of fluorescence intensity was observed.

Another weakness of the change-in-fluorescence-intensity format is that the range of changes of the fluorescence signal is very limited. In the most favorable cases, the observed quenching was 60–70%, whereas in the majority of the cases reported the observed quenching (or enhancement) was less than or equal to 30%. While 60–70% quenching is sufficient for a practical assay, less than or equal to 30% quenching is not large enough for practical applications. Furthermore, fluorescence-quenching assays are limited in the selection of useful fluorescence probes. In many applications it is advantageous to be able to use a variety of fluorescent colors, which allows for the use of signal enhancement or the ratio between signals at different wavelengths.

Another type of fluorescence-based detection assay, called fluorescence polarization, has also been extensively used for the detection of protein-DNA complex formation (see Heyduk, T., and Lee, J. C. *Proc. Natl. Acad. Sci USA* 87, 1744–1748, 1990, which is herein incorporated by reference). The physical basis of this approach is that the fluorescence polarization signal of a macromolecule labeled with a fluorochrome depends on the size of the macromolecule (Lakowicz, J. R. *Principles of Fluorescence Spectroscopy*, Kluwer Academic/Plenum Press, New York, 1999, herein incorporated by reference). Hence, upon the formation of a protein-DNA complex from the protein and DNA components, a larger molecular entity is created, which has an altered fluorescence signature. The use of fluorescence polarization to detect protein-DNA complexes is described in Royer (1998, U.S. Pat. No. 5,756,292), which is herein incorporated by reference. The limitations of the fluorescence polarization approach include the small dynamic range of fluorescence polarization change, the applicability to only relatively short DNA molecules, and the susceptibility to artifacts due to light scattering. Furthermore, fluorescence polarization requires the use of specialized instrumentation and, as in the method described above, the outcome of the fluorescence polarization experiment is sometimes difficult to predict. For example, Hill and Royer (*Methods in Enzymol.* 278, 390–416, 1997, which is herein incorporated by reference) describe an experiment in which no change in fluorescence polarization signal was detected even though the formation of the protein DNA complex had been shown by other techniques.

A third fluorescence-based assay for the detection of the protein-DNA complex formation is resonance energy transfer (FRET) (Stryer, L *Ann. Rev. Biochem.* 47, 819–846, 1978, which is herein incorporated by reference). FRET is based upon the transfer of emitted light energy from a fluorochrome (fluorescent donor) to an acceptor molecule (fluorescent acceptor), which may also be a fluorochrome. The FRET assay is based on the difference in the proximity between DNA labeled with one fluorochrome and the protein labeled with another fluorochrome, wherein the physical proximity between the two fluorochromes in the protein- DNA complex is greater than between the free protein and free DNA. Several published reports illustrate the use of this approach to detect and study protein-DNA interactions (see Kane, S. A., Fleener, C. A., Zhang, Y. S., Davis, L. J., Musselman, A. L., and Huang, P. S. *Anal. Biochem.* 278, 29–39, 2000, which is herein incorporated by reference). The major limitation of the FRET approach is that both the DNA and the protein need to be modified with fluorescence probes.

In summary, luminescence or fluorescence-based assay systems are an attractive tool for detecting DNA binding proteins. However, a general, inexpensive, simple, multi-color fluorescence or luminescence method for detecting sequence specific DNA binding proteins which would be compatible with high-throughput detection formats is currently not available.

SUMMARY OF THE INVENTION

Disclosed are methods of detecting and quantifying DNA binding proteins based upon proximity-based luminescence transfer. In one embodiment of the invention, two double-stranded oligonucleotides are synthesized or isolated, such that, by combining the two double-stranded oligonucleotides, a complete DNA element is formed across the juncture of the oligonucleotides (see FIG. 1A). The DNA binding element comprises a cognate sequence for the binding of DNA binding factors. The first oligonucleotide is labeled with a fluorophore, which is hereafter referred to as the "fluorescent donor", and the second oligonucleotide is labeled with a fluorescent quenching molecule, which is hereafter referred to as "fluorescent acceptor", wherein said quenching molecule may be another fluorophore of a lower excitation wavelength than the first fluorophore. The fluorescent-labeled oligonucleotides are mixed with a sample, which contains a DNA binding factor. Upon mixing, the DNA binding factor associates with both portions of its cognate DNA element, thereby stabilizing the association of the two oligonucleotides. When the two oligonucleotides are in close proximity, the fluorescent donor of the first oligonucleotide transfers its emitted light energy to the fluorescent acceptor of the second oligonucleotide, resulting in the quenching of the emitted light from the fluorescent donor. Fluorescence is measured using standard spectrophotometric or fluorometric methods that are well known in the art. The quenching of the fluorescent signal is correlated with the association of the DNA binding factor to the cognate DNA element.

Given that fluorescence and fluorescence quenching can be routinely measured with accuracy and precision, the present invention is used to quantify the amount or specific activity of a DNA binding factor in a sample, quantify the dissociation constant or affinity of a DNA binding factor, as well as detect the presence of a DNA binding factor in a sample by measuring the change in fluorescence wavelength or intensity.

In one embodiment, the labeled oligonucleotides that comprise a DNA binding element (also known as nucleic acid components) are in solution and free to diffuse in all directions. In another embodiment, said oligonucleotides are affixed to a solid phase substrate, such as, for example, a microtiter plate, microarray slide, membrane or microsphere. In another embodiment, each pair or set of matched oligonucleotides are connected via a linker molecule, wherein the first oligonucleotide is linked to the second oligonucleotide by way of a linker molecule attached to the end of each oligonucleotide, which end is distal to the DNA binding element or fluorescently tagged end of each oligonucleotide. The linked oligonucleotide pairs may be affixed to a solid phase substrate, such as a microtiter plate, membrane, microarray device or microsphere, or they may be free to diffuse in solution.

In another embodiment, a single polynucleotide is labeled in two positions, with a fluorescent donor at the first position and with a fluorescent acceptor at the second position, wherein the fluorescent labels are at such a distance from one another so as not to interact spectroscopically in the absence of a bridging DNA binding factor. In one aspect of this embodiment a portion of a DNA element is located near the first position and another portion of the same DNA element is located near the second position. Upon the binding of a DNA binding factor to both portions of said element, the first position is brought into proximity to the second position, thereby facilitating or stabilizing the spectroscopic interaction between fluorescent donor and fluorescent acceptor. In another aspect of this embodiment, a first DNA element is located at or near the first position and a second DNA element is located at or near the second position. Upon the binding of a DNA binding factor or complex assembly of DNA binding factors (as in an enhanceosome, for example) to the first and/or second element, the first position is brought into proximity to the second position, thereby facilitating or stabilizing the spectroscopic interaction between fluorescent donor and fluorescent acceptor, resulting in a measurable change in fluorescence due to fluorescent energy transfer or quenching.

Any method of proximity-based luminescence detection can be used in the present invention. Embodiments of proximity-based or coincident-based luminescence detection methods include, but are not limited to fluorescence energy transfer, luminescence resonance energy transfer, fluorescence cross-correlation spectroscopy, flow cytometry, direct quenching, ground-state complex formation, chemiluminescence energy transfer, bioluminescence energy transfer and excimer formation. It is understood that the skilled artisan would recognize alternative proximity-based luminescence detection methods that are applicable to the present invention and are herein included in this invention.

Any fluorophore may be used as a fluorescent donor or acceptor in the present invention, however it is preferred that the acceptor excitation wavelength matches the emission wavelength of the donor. In another embodiment, a quencher molecule may be used as a fluorescence acceptor, wherein no light is emitted from the quencher upon excitation. Examples of fluorophores and quenchers are included in the group consisting of Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-diethylaminocoumarin-3-carboxylic acid, Fluorescein, Oregon Green 488, Oregon Green 514, Tetramethylrhodamine, Rhodamine X, Texas Red dye, QSY 7, QSY33, Dabcyl, BODIPY FL, BODIPY 630/650, BODIPY 650/665, BODIPY TMR-X, BODIPY TR-X, Dialkylaminocoumarin, Cy5.5, Cy5, Cy3.5, Cy3, DTPA (Eu3+)-AMCA and TTHA(Eu3+)-AMCA. It is understood that the skilled artisan would recognize that any compatible fluorescence donor/acceptor pair will work in the present invention and that the aforementioned fluorophores and quenchers are exemplary and not limiting.

In another embodiment, it is envisioned that, in addition to luminescence-based proximity assays, flow cytometry, or colorimetric enzyme-based assays may be used to detect binding of a DNA binding factor to a cognate DNA element.

In fluorescence assisted cell sorting, one nucleic acid component is coupled to a bead or microsphere and the other nucleic acid component is coupled to a luminescent molecule or fluorochrome.

In another embodiment, the present invention is used to diagnose and or characterize disease states by profiling the activity of various diagnostic DNA binding proteins in a sample obtained from a patient. It is envisioned that some diseases involve the misexpression of DNA binding factors. For example, some cancers involve the overexpression of transcription factors such as c-myc, c-fos, c-jun, rel or erbA (see Genes IV by Lewin, p. 890), while other cancers, for example some types of breast cancer or colorectal cancers, underexpress DNA repair enzymes. In this embodiment, biopsy samples are combined with labeled oligonucleotides or nucleic acid components, as herein described above, to assay for the presence, absence or specific activity of specific DNA binding factors.

In another embodiment, the present invention is directed to a method of detecting and/or quantifying cell regulatory factors in a sample, wherein said cell regulatory factors act as cofactors or coenzymes that facilitate or abrogate the association of DNA binding factors to cognate DNA elements. A test sample that may contain a regulatory factor is combined with a mixture or kit comprising the labeled oligonucleotides or polynucleotides of the present invention (supra) and the cognate DNA binding factor, wherein the DNA binding activity of the DNA binding factor depends fully or in part on the presence or absence of said regulatory factor. It is envisioned that if the DNA binding factor requires the presence of said regulatory factor in order to bind to the cognate DNA element, fluorescence energy transfer or quenching will occur when the regulatory factor is present in the sample. It is likewise envisioned that if said regulatory factor interferes with the binding of the DNA binding factor to its cognate DNA element, fluorescence energy transfer or quenching will not occur.

In another embodiment, the present invention is drawn to a method of identifying agents or drugs that affect the binding of DNA binding factors to DNA elements. In a situation analogous to the method of detecting and/or quantifying cell regulatory factors in a sample (supra), prospective agents or drugs are combined with various sets of DNA binding factors and labeled oligonucleotides or nucleic acid components comprising cognate DNA elements. In the event that the agent or drug inhibits or disrupts interaction of the DNA binding factor with the DNA element, no change in fluorescence would be measured. In the event that the agent or drug augments the binding of the DNA binding factor to the DNA element, an enhancement of the fluorescence energy transfer or change in fluorescence would be measured.

In another embodiment, the invention is drawn to an array device comprising multiple pairs of labeled oligonucleotides affixed to a solid matrix or suspended in solution in a linear or multidimensional format. Cognate pairs of labeled oligonucleotides, wherein each oligonucleotide comprises a portion of a DNA element that is a binding site for a DNA binding factor and the first label is a fluorescent donor molecule or a chemiluminescent or calorimetric substrate and the second label is a fluorescent acceptor or catalyst for the chemiluminescent or calorimetric substrate, are affixed to a specific position on a solid substrate or suspended within a specific well of a multi-well plate. The solid substrate may be a membrane, such as, for example nitrocellulose, nylon or polyvinyidifluoride ("PVDF"), a multi-well plate or another convenient substrate that lends itself to this purpose. In another aspect of this embodiment, each cognate oligonucleotide pair is linked together by way of a linker molecule affixed to the end of each oligonucleotide distal to the label and DNA element or portion thereof. The linked oligonucleotide pairs are affixed to the solid matrix in a specific array format or are placed within specific wells of a multi-well plate. In another aspect of this embodiment, the array device comprises several nucleic acid components displayed in an array format, wherein each polynucleotide comprises one or several DNA elements that are labeled, wherein the first label is a fluorescent donor molecule or a chemiluminescent or colorimetric substrate and the second label is a fluorescent acceptor or catalyst for the chemiluminescent or calorimetric substrate. Each specific polynucleotide is affixed to a specific position on a solid substrate or suspended within a specific well of a multi-well plate, as described for the oligonucleotide pairs (supra).

The above summary describes in brief the preferred embodiments of the present invention and is not intended to limit the scope of the invention to these described embodiments. The skilled artisan will recognize that there are other possible embodiments of this invention which utilize the general principle of proximity chemical reactions to identify agents that are involved in DNA binding.

DETAILED DESCRIPTION OF THE INVENTION

Definitions

Figure 1:
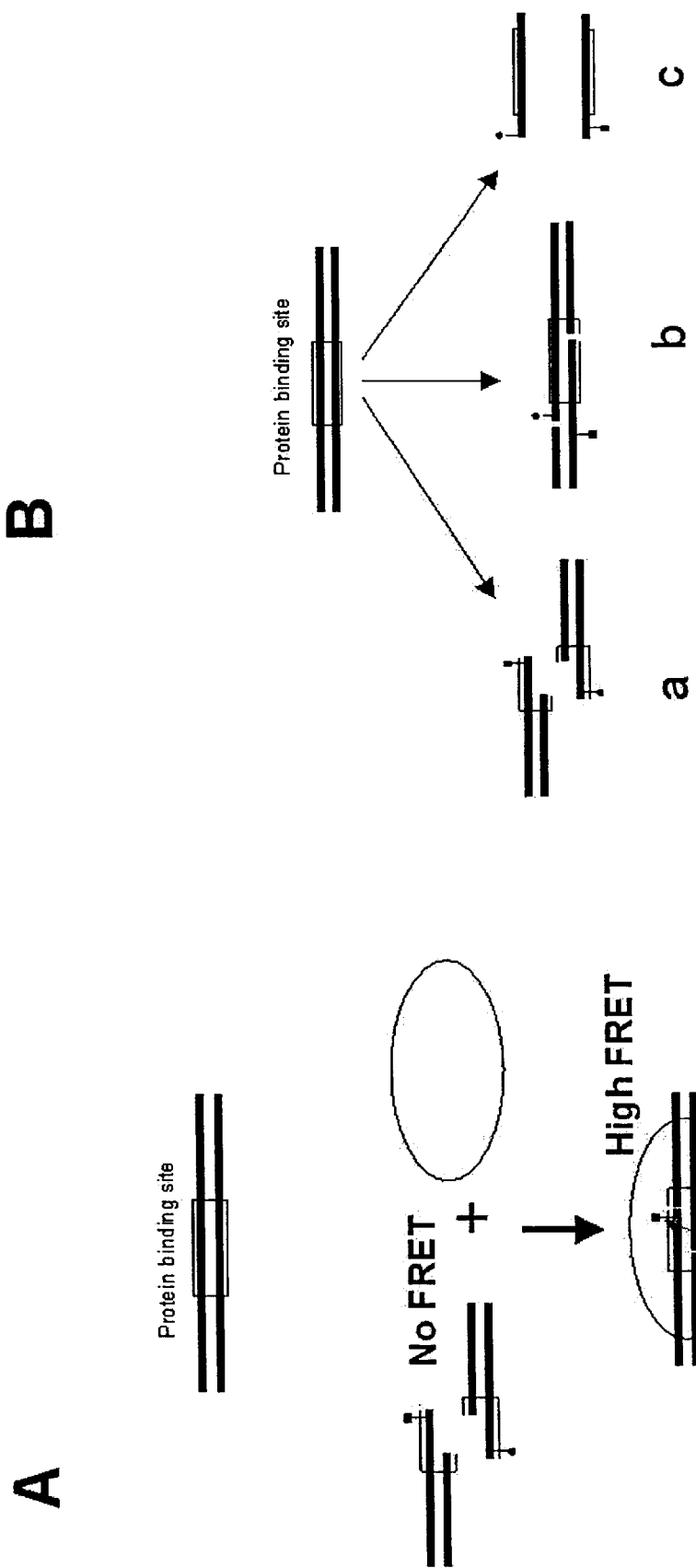
FIG. 1 depicts the overall design of the proximity-based DNA-binding-protein detection method as herein described.

Unless defined otherwise, all technical and scientific terms used herein have the same meaning as commonly understood by one of ordinary skill in the art to which this invention belongs. Although any methods or materials similar or equivalent to those described herein can be used in the practice or testing of the present invention, the preferred methods and materials are described. For the purposes of the present invention, the following terms are defined below.

As used herein, "label" refers to any compound attached to a nucleotide or nucleotide polymer, wherein the attachment may be covalent or non-covalent. Preferably, the label is detectable and renders said nucleotide or nucleotide polymer detectable to the practitioner of the invention. More preferably, the label is a luminescent molecule, chemiluminescent molecule, fluorochrome, fluorescent quenching agent, colored molecule, radioisotope or scintillant. Most preferably the label is a fluorochrome or fluorescent-quenching agent. The term "probe" is for all intents and purposes of this invention, equivalent to the term "label".

As used herein, the term "luminescence" or "luminescent" means any process of light emission, including fluorescence, phosphorescence, scintillation, chemiluminescence and bioluminescence.

As used herein, "fluorochrome" refers to a fluorescent compound which emits light upon excitation by light of a shorter wavelength than the light which is emitted. The term "fluorescent donor" or "fluorescence donor" refers to a fluorochrome which emits light that is measured in the assays described in the present invention. More specifically, a fluorescent donor provides light that is absorbed by a fluorescence acceptor. The term "fluorescent acceptor" or "fluorescence acceptor" refers to either a second fluorochrome or a quenching molecule which absorbs light emitted from the fluorescence donor. The second fluorochrome absorbs the light that is emitted from the fluorescence donor and emits light of longer wavelength than the light emitted by the fluorescence donor. The quenching molecule absorbs light emitted by the fluorescence donor.

It is envisioned that any luminescent molecule, preferably a fluorochrome and/or fluorescent quencher may be used in the practice of this invention, including, for example, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-diethylaminocoumarin-3-carboxylic acid, Fluorescein, Oregon Green 488, Oregon Green 514, Tetramethylrhodamine, Rhodamine X, Texas Red dye, QSY 7, QSY33, Dabcyl, BODIPY FL, BODIPY 630/650, BODIPY 650/665, BODIPY TMR-X, BODIPY TR-X, Dialkylaminocoumarin, Cy5.5, Cy5, Cy3.5, Cy3, DTPA(Eu3+)-AMCA and TTHA(Eu3+)-AMCA.

As used herein, the term "chemiluminescence", "chemiluminescent" or "chemiluminescent substrate" refers to a chemical that produces light as a result of a chemical reaction. Commonly used chemiluminescent substrates include, for example, luminol (5-amino-2,3-dihydro-1,4-phthalazinedione), lophine (2,4,5-triphenylimidazole), lucigenin (bis-N-methylacridinium), other acridinium esters and luciferin-luciferase. For example, in the art recognized ECL™ detection system of Amersham, an acridinium substrate is oxidized by horse radish peroxidase to produce acridinium esters, which react with excess peroxide at an alkaline pH to produce visible chemiluminescence at 430nm.

As used herein, the term "calorimetric" or "colorimetric substrate" refers to a chemical that produces a change in the light absorbance properties as a result of a chemical reaction which produces a colored product. In one art recognized example, p-nitrophenyl phosphate, which when hydrolyzed in the presence of alkaline phosphatase produces p-nitrophenol, which absorbs light at 405 nm (yellow). In another example, p-phenylenediamine plus catechol in the presence of peroxidase and peroxide produces a brownish black product.

As used herein, the term "nucleic acid" refers to an oligonucleotide or polynucleotide, wherein said oligonucleotide or polynucleotide may be modified or may comprise modified bases. Oligonucleotides are generally single-stranded nucleic acid polymers comprising from 2 to 60 nucleotides. Polynucleotides may be either double-stranded DNAs, including annealed oligonucleotides wherein the second strand is an oligonucleotide with the reverse complement sequence of the first oligonucleotide, single-stranded nucleic acid polymers comprising deoxythymidine, single-stranded RNAs or RNA/DNA heteroduplexes.

"Nucleic acid construct" or "nucleic acid component" as used herein generally refers to an annealed pair of complementary single-stranded oligonucleotides which comprise a portion of a DNA binding element, wherein a complete DNA binding element is formed as a result of the combination of two nucleic acid components. A "set of nucleic acid components" as used herein means a matched set of two nucleic acid components which comprise a complete DNA binding element upon association of said two nucleic acid components. It is also envisioned, in some embodiments of the invention, that a nucleic acid component may comprise a single DNA binding element, such that a set of nucleic acid components comprise two or more DNA binding elements that function cooperatively. In such an embodiment, DNA binding factors that bind one or more DNA elements in the presence of transcription factors or other DNA binding proteins may be detected. It is also envisioned that several sets of nucleic acid components can be combined to detect multiple different DNA binding factors. It is also envisioned that multiple sets of nucleic acid components may be assembled into an array, which may then be used to screen multiple different DNA binding factors or analytes.

As used herein, the term "array" means a linear, two-dimensional or three-dimensional display of unique sets of nucleic acid components. It is envisioned that an array may contain sets of nucleic acid components attached to a solid substrate in a discrete pattern, wherein "solid substrate" means a solid, semi-solid or super-cooled liquid surface, substance or matrix. Examples of solid substrates include membranes, plastic microtiter plates, glass slides, chips or microspheres. It is also envisioned that an array may contain sets of nucleic acid components in solution in discrete wells of a microtiter dish.

As used herein, the term "DNA binding element" or "DNA element" refers to a nucleotide sequence which binds to a protein or other moiety. Preferably, the DNA element is a specific nucleotide sequence that binds to a cognate DNA binding protein or factor. The term "cognate" implies a specific recognition between two chemical entities, like, for example a ligand and its cognate receptor or an enzyme and its cognate substrate. Examples of DNA binding elements include promoters, operators, enhancers and silencers, and portions thereof.

As used herein, the term "DNA binding factor" refers to a chemical entity that binds non-covalently to a nucleic acid. In a preferred embodiment, the DNA binding factor is a protein, polypeptide or fragment of a polypeptide that binds to a cognate DNA element, and is hence referred to as a "DNA binding protein". In a most preferred embodiment, the DNA binding factor is a sequence-specific DNA binding protein which directly binds to a specific cognate DNA sequence. In other preferred embodiments, a DNA binding protein or factor is a protein, polypeptide, fragment of a polypeptide or other chemical structure which indirectly binds to a DNA element or associates with other DNA binding proteins to facilitate or abrogate the function of said other DNA binding proteins. It is envisioned that transcription activators, transcription repressors, or other components of enhanceosomes, which don't bind directly to DNA, but bind to other DNA binding factors to effect gene activity, are included within this embodiment.

In another embodiment, DNA binding factors and analytes are contained within a sample taken from a subject. The subject is preferably a human patient suffering from a type of cancer or other disease of genome instability. The subject may also be an animal, a plant, a microorganism or a cell. The sample is preferably an "extract of cellular materials," which contains DNA binding factors and is preferably devoid of interfering or competing DNA binding elements.

It is further envisioned that DNA binding factors or DNA binding proteins may include transcription factors, chromatin remodeling factors and genome maintenance enzymes, among others. A short list and description of the several types of DNA binding factors is described in Benjamin Lewin, Genes VII, Oxford University Press, New York, 2000, which is herein incorporated by reference.

Transcription factors bind to specific cognate DNA elements such as promoters, enhancers and silencer elements, and are responsible for regulating gene expression. Transcription factors may be activators of transcription, repressors of transcription or both, depending on the cellular context. Transcription factors include, for example, p53, c-myc, c-jun, c-myb, c-fos, c-rel, c-erbA, E2F, β-catenin, cAMP receptor protein ("CAP"), Lac repressor ("LacR"), steroid receptors, homeodomain proteins, POU domain proteins, helix-turn-helix transcription factors, basic helix-loop-helix transcription factors ("bHLH"), basic leucine zipper transcription factors ("bZip"), zinc finger transcription factors and nuclear hormone receptors.

Components of enhanceosomes comprise a subset of transcription factors. As used herein, the term "enhanceosome" refers to a large nucleoprotein complex assembled from several transcription factors cooperatively bound to multiple binding sites in an enhancer. An important component of enhanceosomes is HMG-1, a DNA binding protein that binds to the minor groove of DNA and facilitates bending of the DNA. Enhanceosome proteins include, for example, DNA-bending proteins, HMG box-containing proteins, SRY, LEF-1, HMG-1, HMG-2, transcription factors and basal transcription factors.

As used herein, "basal transcription factors" refer to RNA polymerase 11 and its associated factors, which are generally recognized in the art. Basal transcription factors include RNA polymerase II , TFIID, TFIIA, TATA-binding protein, TFIIB, TFIIF, TFIIE, TATA-binding protein-associated factors, NTF-1 and Sp1.

Chromatin-remodeling factors are involved in the maintenance of heterochromatin (or other regions of transcriptionally inactive genes) and euchromatin (or other regions of transcriptionally active genes). They are also involved in the global silencing of stretches of chromosomes and phenomena such as genetic imprinting. Chromatin-remodeling proteins include, for example, nucleosome proteins (e.g., histones), histone acetyltransferases ("HATs"), histone deacetylases ("HDACs"), DNA methyltransferases, nucleoplasmins, HMG proteins, repressor complex proteins, polycomb-related factors and trithorax-related factors, components of the SWI/SNF complex, components of the Sin3 repressor complex, components of the RSC complex, components of the NURF complex, components of the Pc-G complex, components of the trxG complex, CpG methylases, MeCP1 and MeCP2.

Genome-maintenance enzymes are DNA binding proteins and other proteins useful in the repair of damaged DNA, faithful replication of DNA or exchange of genetic information during recombination. They include, for example, DNA polymerases, RNA polymerases, base-excision repair enzymes, nucleotide-excision repair enzymes, homologous recombination enzymes, end joining enzymes, mismatch repair enzymes, exonucleases, endonucleases, double-strand break repair enzymes, single-strand break repair enzymes, transcription-coupled repair enzymes, ligation enzymes, translesion synthesis enzymes and enzymes involved in telomere metabolism. For the purposes of this invention, p53 is considered to be a genome-maintenance enzyme as well as a transcription factor, due to its role as a cell cycle check point gene product.

As used herein, the term "activity of a DNA binding factor" includes the specific activity or quantity of the DNA binding factor in a sample and the affinity of the DNA binding factor for a cognate DNA binding element.

As used herein, the term "linker" or "linker molecule" refers to any polymer attached to a set of two nucleic acid components, wherein the set of two nucleic acid components comprise a complete DNA binding element and wherein the attachment may be covalent or non-covalent. It is envisioned that the linker can be a polymer of amino acids or nucleotides. A preferred linker molecule is flexible and does not interfere with the binding of a DNA binding factor to the set of nucleic acid components. A preferred linker molecule is comprised of 12 moieties of the Spacer 18 phosphoramidate (Glen Research, Sterling, Va.), the structure of which is shown in FIG. 11B.

As used herein, the term "analyte" refers generally to a chemical moiety, which may be an ion or molecular compound which mediates the association of a DNA binding factor to a nucleic acid element. Analytes also include secondary messenger molecules such as, for example, calcium ion, cAMP and IP3. Analyte also refers generally to cellular events, such as, for example, phosphorylation, lipidation or other post-translational modifications, association with or dissociation from adapter molecules, or proteolysis events that affect the binding of DNA binding factors to nucleic acid elements. Analyte also refers to any drug, agent, reagent, prospective drug, prospective agent or prospective reagent which mediates the association of a DNA binding factor to a nucleic acid element. "Mediation of association" means the abrogation of binding, either partial or full, or facilitation of binding, either partial or full.

Description of the Embodiments of the Invention

Methods for detection of DNA binding proteins and for measurement of their DNA binding activity are disclosed. At the heart of the invention is the idea of preparing two nucleic acid molecules such that the sequence corresponding to a cognate protein-binding site is split between these two nucleic acid molecules. The two nucleic acid molecules (also referred to as nucleic acid components) may also contain a short complementary overhang such that the nucleic acid components have some propensity to associate but this propensity is designed to be low so that in the absence of the protein very little association between the nucleic acid components occurs. The association between the two nucleic acid components re-creates the cognate binding site for the protein so that in the presence of the protein, the affinity of the protein to its cognate nucleic acid binding site will drive the association of the two nucleic acid components to completion. Detection of protein-DNA complex formation is accomplished by labeling each of the two nucleic acid components with luminescent probes, fluorochromes, chemiluminescent substrates or calorimetric substrates. The physical proximity between the two nucleic acid fragments in a protein-DNA complex provides the mechanism for a change in fluorescence signal or formation of a colorimetric/chemiluminescent product associated with protein-DNA complex formation.

In another embodiment of the invention, one of the nucleic acid components may be attached to a bead (microsphere) and the other nucleic acid component may be labeled with a luminescent or fluorescent probe. In the presence of a cognate DNA binding factor, a protein-DNA complex forms, such that the bead or microsphere is labeled with the luminescent probe. The labeled bead or microsphere may be detected using art recognized fluorescence activated cell sorting or flow cytometric devices. This embodiment represents a coincidence-based luminescence signal detection method. For the purposes of this invention, the term "proximity-based" is meant to include coincidence-based.

Any proximity-based (which includes by definition coincidence-based) luminescence signal detection method such as FRET (Stryer, L.Ann. Rev. Biochem. 47, 819–846, 1978), fluorescence cross-correlation spectroscopy ("FCCS") (Maiti et al., Proc. Nat'l Acad Sci USA 94, 11753–11757, 1997), flow cytometry (Nolan and Sklar, Nature Biotechnology 16:633–638, 1998), scintillation proximity ("SPA") (Hart and Greenwald, Molecular Immunology 16:265–267, 1979; U.S. Pat. No. 4,658,649), luminescence resonance energy transfer (LRET) (Mathis, G. Clin. Chem. 41, 1391–1397, 1995), direct quenching (Tyagi et al., Nature Biotechnology 16, 49–53, 1998), ground-state complex formation (Packard, B. Z., Toptygin, D. D., Komoriya, A., and Brand, L. Biophys. Chem. 67, 167–176, 1997), chemiluminescence energy transfer (CRET) (Campbell, A. K., and Patel, A. Biochem. J. 216, 185–194, 1983), bioluminescence resonance energy transfer (BRET) (Xu, Y., Piston D. W., Johnson, Proc. Natl. Acad. Sci., 96, 151–156, 1999), or excimer formation (Lakowicz, J. R. Principles of Fluorescence Spectroscopy, Kluwer Academic/Plenum Press, New York, 1999) is compatible with the design of the assay. Furthermore, it is envisioned that any chemiluminescent or colorimetric assay, such as, for example, the art recognized alkaline phosphatase-NBT/BCIP system, may be used in the present invention. It is further envisioned that the invention is applicable to any DNA binding protein, since the invention is based on the general property of all such DNA-binding proteins rather than on a feature specific to a given protein. The invention offers great flexibility of signal detection mode and nature of the fluorescence probe used. Multicolor detection is readily possible.

According to the invention as mentioned above, FCCS detection involves measuring the fluctuation of the fluorescence intensity signal in a sample containing the two nucleic acid components, wherein each nucleic acid component is labeled with a fluorochrome with a different emission wavelength. The association of the two fluorochrome-labeled nucleic acid components in the presence of a cognate DNA binding factor protein may be measured by detecting the cross-correlation between each of the signals corresponding to the two fluorochromes. The use of FCCS for detection of association between two macromolecules labeled with two different fluorochromes is described in Rippe, K., "Simultaneous Binding of Two DAN duplexes to the NtrC-Enhancer complex Studied by Two-Color Fluorescence Cross-Correlation Spectroscopy," Biochemistry 39, 2131–2139, 2000, which is incorporated herein by reference.

According to the invention as mentioned above, flow cytometry may be used to detect the association of a luminescent or fluorescent-labeled nucleic acid component to a the "target" nucleic acid component, which is immobilized on a surface of microsphere. The use of flow cytometry in a similar situation is described in Nolan, J. P., andSklar, L. A., "The emergence of flow cytometry for sensitive, real-time measurements of molecular interactions," Nature Biotechnology 16, 633–638, 1998, which is incorporated herein by reference. In one embodiment, one nucleic acid component is attached to a microsphere, wherein said nucleic acid component may or may not be labeled with one fluorochrome and wherein the microsphere is preferably several microns in diameter. The second nucleic acid component may be labeled with a fluorochrome, wherein the is of a different color if the microsphere-attached nucleic acid component was also labeled. The association between the two nucleic acid components in the presence of a cognate DNA binding factor may be measured using flow cytometry as a change in particle fluorescence or the ratio between fluorescence at two different colors if both nucleic acid components were labeled with fluorochromes.

According to the invention as mentioned above, it is envisioned that a scintillation proximity assay ("SPA") may be employed to determine DNA binding factor activity. In one embodiment, one nucleic acid component is attached to a microsphere that contains a solid scintillant and the other nucleic acid component is labeled with a radioisotope, preferably tritium. In the presence of the cognate DNA binding factor, the radioisotope label is brought into close proximity of the microsphere containing the scintillant, thereby inducing the emission of light from the scintillant. The light may be detected by art recognized means of scintillation detection. The method of SPA is described in Hart and Greenwald, *Molecular Immunology* 16:265–267, 1979 and U.S. Pat. No. 4,658,649, which are both incorporated herein by reference.

In other embodiments, the invention provides means for rapidly determining the physical parameters of the protein-DNA complex formation such as dissociation constants. The invention also provides a means for determining the affinity of a DNA binding factor for variant DNA binding elements. In this embodiment, nucleic acids comprising variant DNA binding elements are combined with a DNA binding factor and its cognate labeled nucleic acid components. It is envisioned that those variant DNA binding elements that compete for the DNA binding factor will affect the luminescence signal output compared to controls.

Furthermore, given that the DNA binding activity of many proteins is regulated by other molecules or analytes, such as cAMP or IP3, for example, the invention also provides means for detecting these other molecules or analytes. Likewise, it is envisioned that the invention may also be used as a platform to identify novel agents, other analytes and molecules, or drugs that mediate protein-DNA interactions. It is also envisioned that the invention may be used to identify proteins comprising an enhanceosome or supernumerary chromatin structure, wherein the proteins do not directly bind to DNA but rather bind directly or indirectly to other DNA binding proteins.

FIG. 1A illustrates the basic idea for detecting sequence-specific DNA binding proteins as described in this invention. In a preferred embodiment of the invention, two nucleic acid fragments (components) are prepared wherein each fragment contains a portion of a nucleic acid sequence corresponding to a cognate binding site for a protein. FIG. 1B illustrates examples of several different possibilities of designing such molecules. In one aspect of the invention, the two nucleic acid fragments contain short complementary overhangs, which provide some affinity for the two fragments to anneal. In an alternative aspect of the invention, which is envisioned to be useful for proteins that can bind efficiently to a short DNA sequence, i.e., equal to or less than 10 base pairs (bp), the two nucleic acid fragments correspond to the two single-stranded components of the nucleic acid duplex (FIG. 1B, design option "c"). The length of the overhang in design options "a" and "b", or the length of single-stranded oligonucleotides in design "c" (FIG. 1B) determines the propensity of the two nucleic acid molecules to associate in the absence of the cognate protein and is chosen such that at the concentrations of the nucleic acid fragments used in the assay the efficiency of spontaneous re-annealing is very low. Thus, in the absence of the cognate protein very little association between the two DNA molecules occurs. In the presence of the cognate protein, the affinity of the protein for the nucleic acid drives the annealing of the two nucleic acid fragments and a specific protein-DNA complex is formed. Re-annealing of nucleic acid fragments will bring the two labels or fluorochromes into close proximity and this protein-induced close proximity is utilized to generate a change in luminescence signal or production of a colored product, which thereby indicates the formation of a protein-DNA complex.

The physical basis of the preferred embodiment of the invention is a fundamental relationship between the free energy ($\Delta G^0$) for the formation of protein-DNA complex and the equilibrium binding constant (K) describing the amount of protein-DNA complex formed at any given concentration of protein and nucleic acid:

$$\Delta G^0 = -RT \ln K \qquad (eq.1)$$

If the free energy for binding of the protein to its cognate nucleic acid site is $\Delta G^0$, splitting the cognate binding site into two "half-sites" in two separate DNA fragments, as illustrated in FIG. 1A, will result in the free energy of binding to a half-site being roughly ½ of $\Delta G$. Since the equilibrium constant (K) and free energy ($\Delta G^0$) are related by a logarithmic relationship (eq. 1), reducing the binding free energy by two-fold will result in a decrease in the binding constant by several orders of magnitude. Thus, under conditions where efficient binding of a protein to its cognate full-site occurs, no detectable binding of the protein to the half-site should occur. This large difference in the affinity of the protein to the full-site compared to the half-site is the driving force for the re-annealing of the two nucleic acid half-sites in the presence of the protein.

Figure 2:
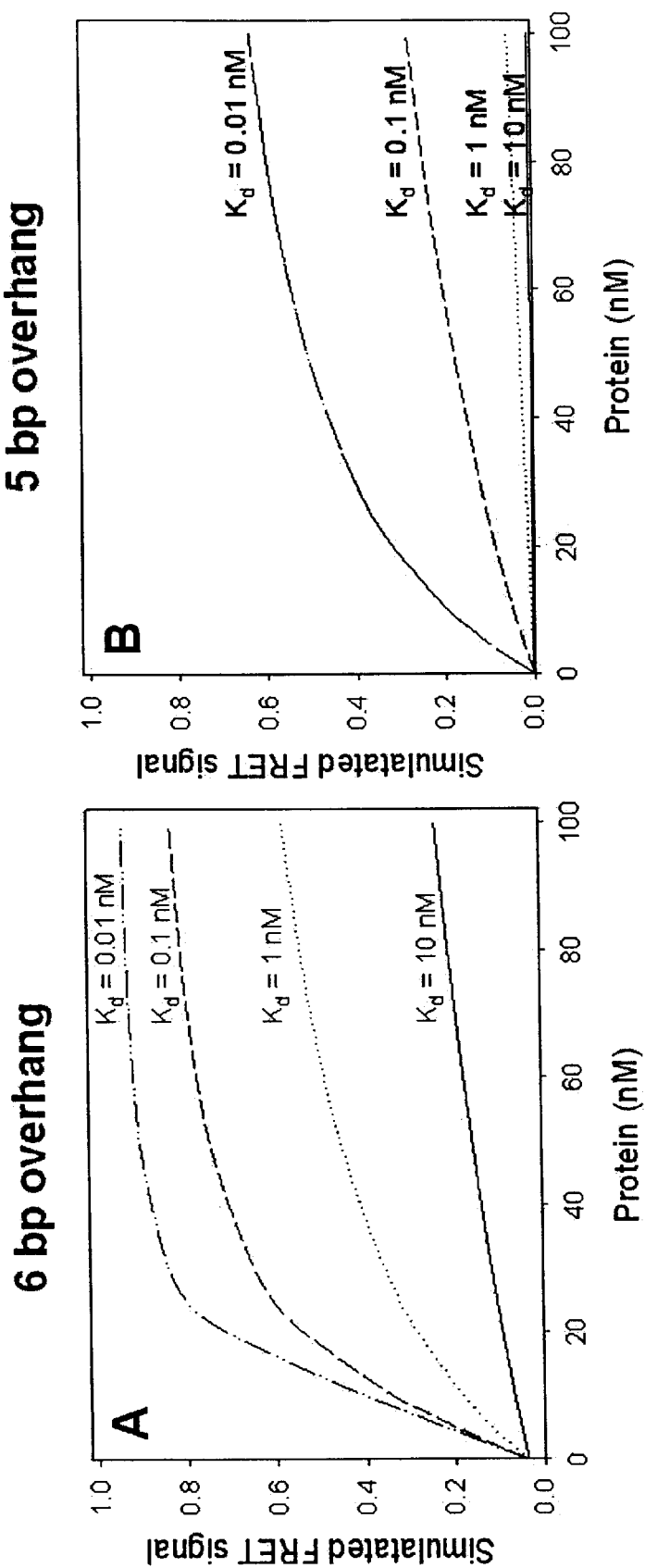
FIG. 2. shows theoretical simulations of the expected fluorescence signal change in the presence of DNA binding protein for the design illustrated in FIG. 1.

Whereas this invention is not bound by theoretical considerations, the following reaction scheme describes the behavior of the detection system depicted in FIG. 1:

where DNA-A is the acceptor-labeled DNA half-site, DNA-D is the donor-labeled DNA half-site, P is the DNA binding protein, $K_1$ is the equilibrium constant for the annealing of DNA-A and D-DNA fragments, and $K_D$ is the equilibrium constant for binding of protein P to its cognate DNA binding site. The results of the calculations for two different lengths of the complementary overhangs are shown in FIG. 2, wherein the length of the overhang determines the value of $K_1$. These simulations demonstrate the feasibility of the basic design of the invention described herein and depicted in FIG. 1, and that easily measurable changes in an observable signal, whether that change in signal is due to fluorescence energy transfer or production of a chemiluminescent or colored product, will be detected with a wide range of equilibrium constants typically observed for DNA binding proteins. Thus, the general applicability of this invention to any DNA binding protein is a result of it being based on the general property of all DNA binding proteins, that general property being the high affinity for binding to a complete cognate binding site, and on the general thermodynamic logarithmic relationship between the free energy of the interaction and the equilibrium binding constant.

The present invention offers extensive flexibility in the use of variety of luminescent or colorimetric probes, in the selection of sites for attachment of said probes within the nucleic acid molecules, and in the selection of a particular method of signal generation and detection. Commercially available reagents allow the incorporation of a variety of probes into the 5' end, 3' end or internal positions of the oligonucleotides during automated oligonucleotide synthesis. It is therefore possible to incorporate probes during oligonucleotide synthesis or probes may be attached to the oligonucleotides via post-synthetic modification of oligonucleotides derivatized with reactive amino or thiol groups. The present invention does not impose any restrictions regarding the nature and the position of the probe as long as the probe does not interfere with the formation of protein-nucleic acid complex. As illustrated in FIG. 1B, several alternative embodiments of labeled nucleic acid fragments are possible. For example, for some proteins it may not be possible to use design "a" (FIG. 1B) in which the probes are located within the binding site for the protein and thus could potentially interfere with protein binding. In such a case, one alternative will be to use design "b" (FIG. 1B) in which the probes are located outside the protein binding site.

In another embodiment, oligonucleotides can be labeled with essentially any amino- or thiol reactive luminescent probe of any emission spectra, and thus the color of the luminescence or fluorescence signal in the assay can be selected according to the specific needs of the application. As a result of this capability, it is possible to simultaneously detect two or more proteins within one assay kit using a mixture of DNA constructs designed to recognize different proteins and labeled with luminescent probes exhibiting different emission spectra.

The sensitivity of the detection of DNA-binding proteins using this invention is determined by two factors: sensitivity of luminescence signal detection and affinity of the protein to its DNA binding site. Detection sensitivity of the invention will not likely be limited by the sensitivity of signal detection since, especially in the case of fluorescence detection, commercial instrumentation can routinely detect fluorescence at picomolar fluorochrome concentrations. Also, recent advances in signal detection have resulted in sensitivities sufficient to detect single fluorochrome molecules. Hence, it is more likely that the sensitivity of detection will be determined by the affinity of the protein to its DNA binding site. Therefore, the range of detection of DNA binding proteins will be in the range of the affinity of DNA binding proteins to their cognate DNA binding sites, which is typically from low picomolar to high nanomolar protein concentrations.

The present invention also offers great flexibility in designing the DNA molecules to be used in the detection assay. For example, the length of the DNA molecules is not limited and additional elements may be incorporated into the DNA molecules. In one embodiment, an alternate binding site for a second protein may be incorporated into one of the nucleic acid fragments, wherein the second protein cooperates in binding to the nucleic acid with the protein being assayed. The assay may then be performed in the presence of this second protein, or the assay may be performed in the presence and absence of this second protein to detect differences in the activity of the studied protein induced by the presence of the second protein.

In another embodiment, the DNA components used in the assay are attached to a surface of a solid support. Methods for attaching nucleic acids to solid support are well known in the art and described in the literature (see Rogers, Y. H., et al., Anal. Biochem. 266, 23–30, 1999; Joos, B., et al., Anal. Biochem. 247, 96–101, 1997; Running J A, and Urdea M S, BioTechniques, 8:276277, 1990; which are herein incorporated by reference). Detection of the protein is thus accomplished by monitoring the signal emanating from the surface of solid support. Multiple DNA constructs designed to recognize different proteins may be attached to the solid surface resulting in an array capable of simultaneous detection of many DNA binding proteins. Solid supports may be membranes, such as nitrocellulose, PVDF or nylon, or plastic tissue culture dishes or microtiter plates.

In another embodiment, the nucleic acid components used in the assay may comprise a single nucleic acid molecule, wherein each nucleic acid component is separated by a length of nucleic acid which allows for bending of the entire nucleic acid such that the nucleic acid components may be brought into close proximity. It is envisioned that such a format may be used to detect or identify DNA binding proteins that are involved in higher order chromatin structure or enhanceosome structure, for example.

In another embodiment, the nucleic acid components used in the assay may be linked together via a flexible linker molecule. It is envisioned that the linkage of the nucleic acid components will facilitate the interaction of the protein and the cognate nucleic acid binding site and allow for faster interaction kinetics. Preferred flexible linker molecules are polymers of spacer-18-phosphoramidate moieties, as herein described (infra).

A particular strength of the present invention is that it is simple to operate and is a truly homogenous assay, which requires only mixing of the assay solution, which comprises the nucleic acid components, with a test solution, which comprises a DNA binding protein, analyte or other protein component involved in chromatin or enhanceosome structure, followed by a short incubation and signal detection. No washing or successive additions of other components of the assay are necessary.

In another embodiment, the invention is directed to a method of diagnosing a disease in a patient or subject, wherein the disease is mediated by a DNA binding protein or by a mutation in a cognate DNA binding element. The patient or subject may be a human or other animal. The disease may be due to altered DNA binding proteins, such as, for example breast cancer, which results from alterations in the activity of the DNA repair enzymes BRCA1 or BRCA2. Other examples of diseases and their molecular bases are described in Table 1 (see Hoeijmakers, J. H. J., Nature 411:366–374, 2001, which is herein incorporated by reference). It is to be understood that the diseases and syndromes presented in Table 1 represent a small subset of diseases which may be diagnosed using the present invention. The information presented in Table 1 is for exemplary purposes and therefore can not be construed as limiting.

TABLE 1

Diseases associated with DNA binding protein abnormalities

| DISEASE OR SYNDROME | AFFECTED MOLECULAR MECHANISM |
|---|---|
| ataxia telangectasia (AT) | double-strand break repair |
| AT-like disorder | double-strand break repair |
| Bloom syndrome | homologous repair |
| breast cancer | homologous recombination |
| cancers recalcitrant to radiation therapy | p53 (transcription factor) |
| cockayne syndrome | transcription coupled repair (TCR) |
| hereditary nonpolyposis colorectal cancer | mismatch repair |
| Ligase IV deficiency | end joining |
| Nijmegen breakage disorder | double-strand break repair |

TABLE 1-continued

Diseases associated with DNA binding protein abnormalities

| DISEASE OR SYNDROME | AFFECTED MOLECULAR MECHANISM |
|---|---|
| Rothmund-Thomson syndrome | homologous repair |
| trichothiodystrophy | NER and TCR |
| Werner syndrome | homologous recombination/translesion repair |
| xeroderma pigmentosum | nucleotide excision repair (NER) |
| xeroderma pigmentosum variant | translesion synthesis |

Proteins or other analytes may be extracted from a sample obtained from the patient using standard extraction protocols, which are well known in the art. Samples may be obtained from biopsied tissue, blood cells, skin cells, hair follicle cells, tissue plugs, epithelial cells obtained from the buccal cavity or other tissue sources. Samples may also include plant tissue, cultures of microorganisms or eukaryotic cells. The extracted samples are then mixed with the nucleic acid components of the invention, as herein described, and assayed for DNA binding activity, facilitation of DNA binding activity or abrogation of DNA binding activity.

It is further envisioned that the invention may be used to identify agents or drugs which facilitate the binding of abnormal DNA binding proteins to cognate DNA elements, or conversely, to facilitate the binding of normal DNA binding proteins to abnormal DNA elements. In another embodiment, the invention may be used to identify agents or drugs which disrupt the binding of abnormal DNA binding proteins to cognate DNA elements, or conversely, to disrupt the binding of normal DNA binding proteins to abnormal DNA elements. The term "abnormal" refers to aberrant or mutated forms of the nucleic acid or protein found within a patient, which is no longer able to bind to their respective partner in a physiologically normal manner.

The above disclosure describes several preferred embodiments of the invention, which are not to be interpreted as limiting the scope of the invention. It is envisioned that the skilled artisan in the practice of this invention will recognize other embodiments of this invention which are not overtly disclosed herein. The inventor further stresses that any and all DNA binding proteins, transcription factors, novel drugs, agents and/or analytes which affect DNA-protein interactions may be detected or identified by this invention.

The invention is further illustrated by the examples described below. These examples are meant to illustrate the invention and are not to be interpreted as limiting the scope of the invention.

EXAMPLE 1

Detection of cAMP Receptor Protein (CAP), a Sequence-specific DNA Binding Protein from *E. coli*

Figure 3:
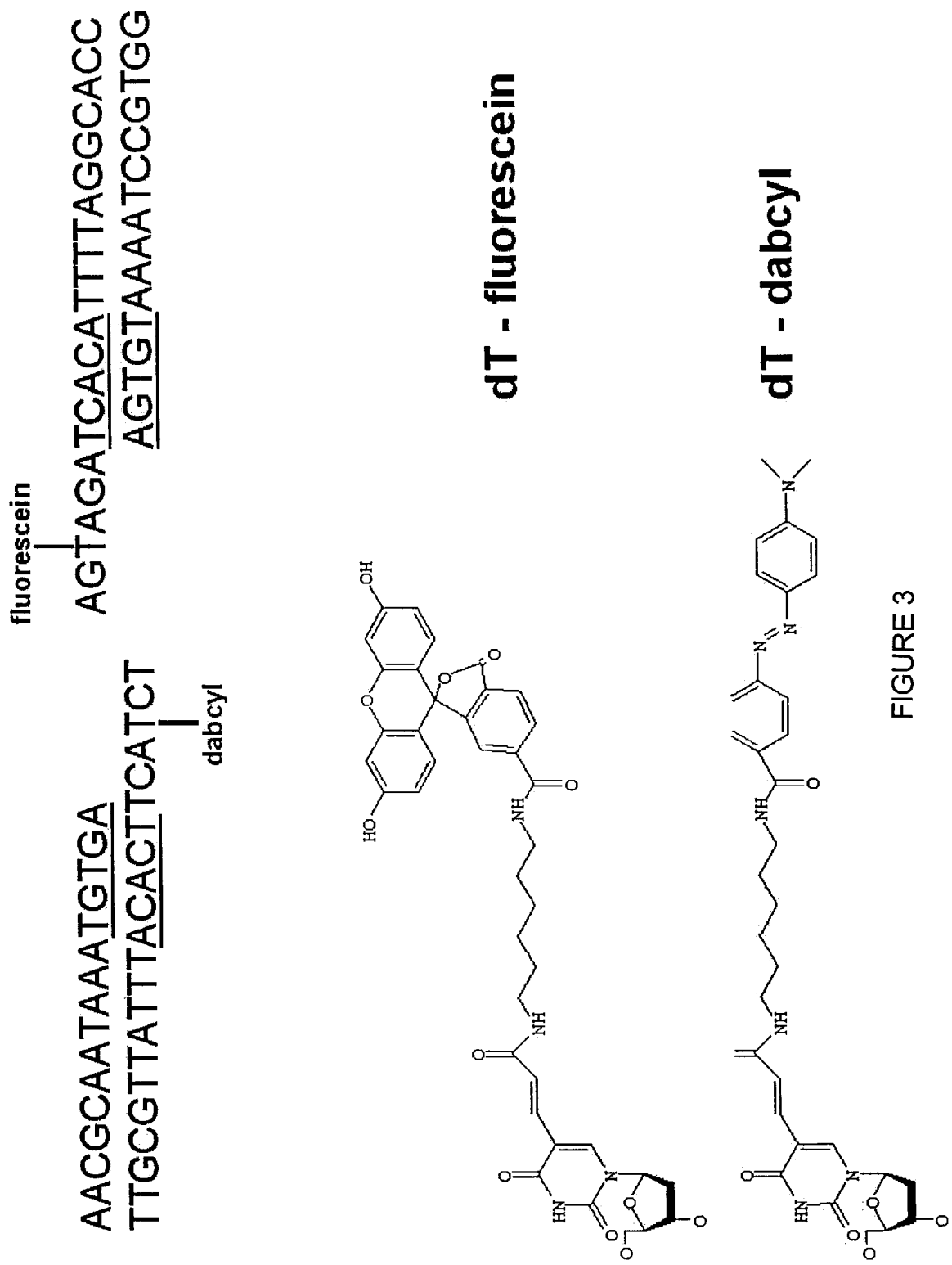
FIG. 3 depicts fluorochrome-labeled oligonucleotides of SEQ ID NO:1 through SEQ ID NO:4 for the detection of CAP protein.

CAP is a bacterial transcription activator which binds DNA at a $K_d$=~0.1 nM in a sequence specific manner (Busby, S., and Ebright, R. H. J. *Mol. Biol.* 293, 199–213, 1999). A 38 bp DNA sequence corresponding to a consensus CAP site (Ebright, R. H., Ebright, Y. W. & Gunasakera, A. *Nucleic Acids Res.* 17, 10295–10305, 1989) was used as a basis for designing oligonucleotides necessary for preparing the CAP assay reagents according to the scheme illustrated in FIG. 1A. FIG. 3 illustrates the details of the design used.

The following four oligonucleotides were synthesized using standard phosphoramidate automated oligonucleotide synthesis (F=dT-fluorescein; D=dT-dabcyl):

5'-MCGCAATAAATGTGA (CAP1; SEQ ID NO:1)

5'-AGFAGATCACATTTAGGCACC 3' (CAP2; SEQ ID NO:2)

5'-GGTGCCTAAAATGTGA (CAP3; SEQ ID NO:3)

5'-TCDACTTCACATTTATTGCGTT (CAP4; SEQ ID NO:4)

The fluorescence donor (fluorescein) and the fluorescence acceptor (dabcyl) were introduced into DNA fragments using commercially available dT-fluorescein and dT-dabcyl (Glen Research, Sterling, Va.), wherein dT stands fordeoxythymidine. The oligonucleotides were purified using reverse phase chromatography on a RPC column (Pharmacia) as previously described (Heyduk, E., and Heyduk, T. *Anal. Biochem.* 248, 216–227, 1997). The fractions containing the oligonucleotides were dried in a vacuum centrifuge concentrator and subsequently dissolved in 50 µl of water. The concentration of the stock solutions of oligonucleotides was determined by recording the UV-VIS absorption spectrum of a small aliquot of the stock solution diluted to 400 µl. The CAP1 oligonucleotide (SEQ ID NO:1) was hybridized with CAP4 oligonucleotide (SEQ ID NO:4) to generate the CAP1/CAP4 duplex and CAP2 oligonucleotide (SEQ ID NO:2) was hybridized with CAP3 oligonucleotide (SEQ ID NO:3) to generate the CAP2/CAP3 duplex. For the hybridization appropriate oligonucleotides were mixed at 10 µM concentration in 100 µl of 50-mM Tris/HCl (pH 8.0), 100 mM NaCl, 1 mM EDTA, heated for 1 min at 95° C. and then cooled to 25° C. for 1 hr. All subsequent fluorescence measurements were performed at 25° C. in 50-mM Tris/HCl (pH 8.0), 100 mM NaCl (or 50 mM NaCl where indicated), 1 mM EDTA, 0.1 mg/ml BSA, and 200 µM cAMP in 200 µl quartz cuvette using Aminco-Bowman Series 2 spectrofluorometer. The excitation wavelength was at 490 nm and the emission was recorded from 500 to 650 nm.

Figure 4:
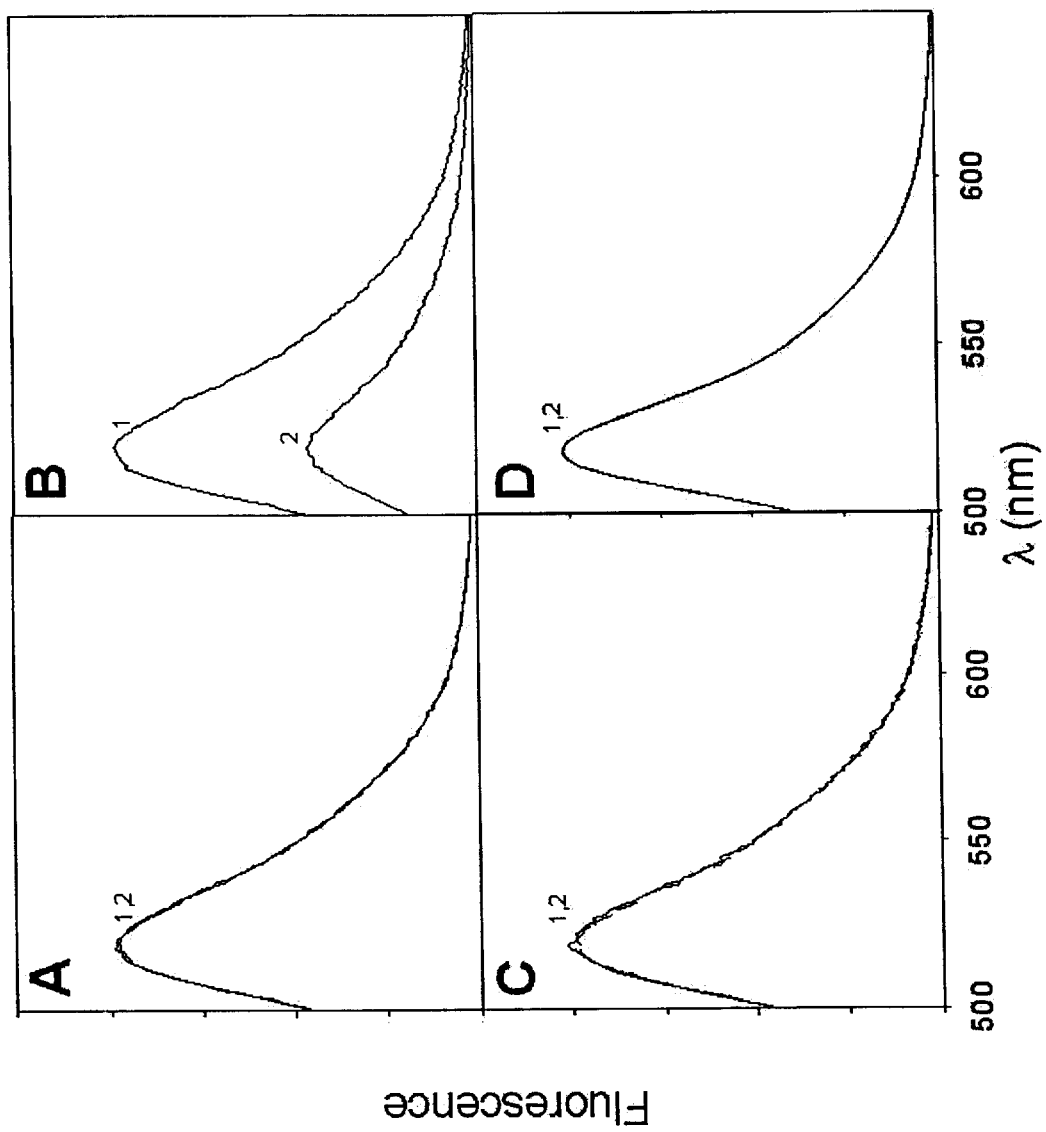
FIG. 4 shows fluorescence spectra of DNA molecules shown in FIG. 3 in the presence of CAP and CAMP (panel B, curve 2), in the absence of CAP (panel A), in the presence of CAP without cAMP (panel C) and in the presence of Trp repressor protein (panel D).

FIG. 4A shows the spectrum of 50 nM of the CAP2/CAP3 duplex (curve 1) and the spectrum of 50 nM of the CAP2/CAP3 duplex in the presence of 50 nM CAP1/CAP4 duplex (curve 2). No significant change of the fluorescence of the CAP2/CAP3 duplex in the presence of the CAP1/CAP4 duplex was observed, indicating that in the absence of CAP protein there is very little association between the CAP2/CAP3 and CAP1/CAP4 duplexes. FIG. 4B illustrates changes in fluorescence observed upon the addition of CAP protein. The spectrum of 50 nM of the CAP1/CAP4 duplex and 50 nM of the CAP2/CAP3 duplex was recorded (curve 1). CAP protein was added at 75 nM and after 15 minutes of incubation the spectrum was recorded (curve 2). A major quenching of fluorescence of approximately 50% of the control signal intensity was observed, which is consistent with the prediction that in the presence of CAP protein the association between the CAP1/CAP4 and CAP2/CAP3 duplexes is facilitated and that the fluorescein (fluorescent donor) present in the CAP2/CAP3 duplex is brought into close proximity to the dabcyl (fluorescent acceptor) present in the CAP1/CAP4 duplex, which results in the quenching of fluorescence emission due to FRET between the fluorescein and dabcyl.

To test the specificity of the fluorescence quenching observed, the experiment illustrated in FIG. 4B was repeated in the absence of CAMP. Sequence-specific binding of CAP requires the presence of CAMP and in the absence of cAMP only non-specific low affinity DNA binding is observed. No change in fluorescence upon addition of CAP in the absence of CAMP was observed (FIG. 4C), further demonstrating the specificity of the assay. Also, no change in fluorescence was observed when an unrelated DNA binding protein, i.e., Trp repressor ("TrpR"), was added at high concentration (400 nM) (FIG. 4D).

Figure 5:
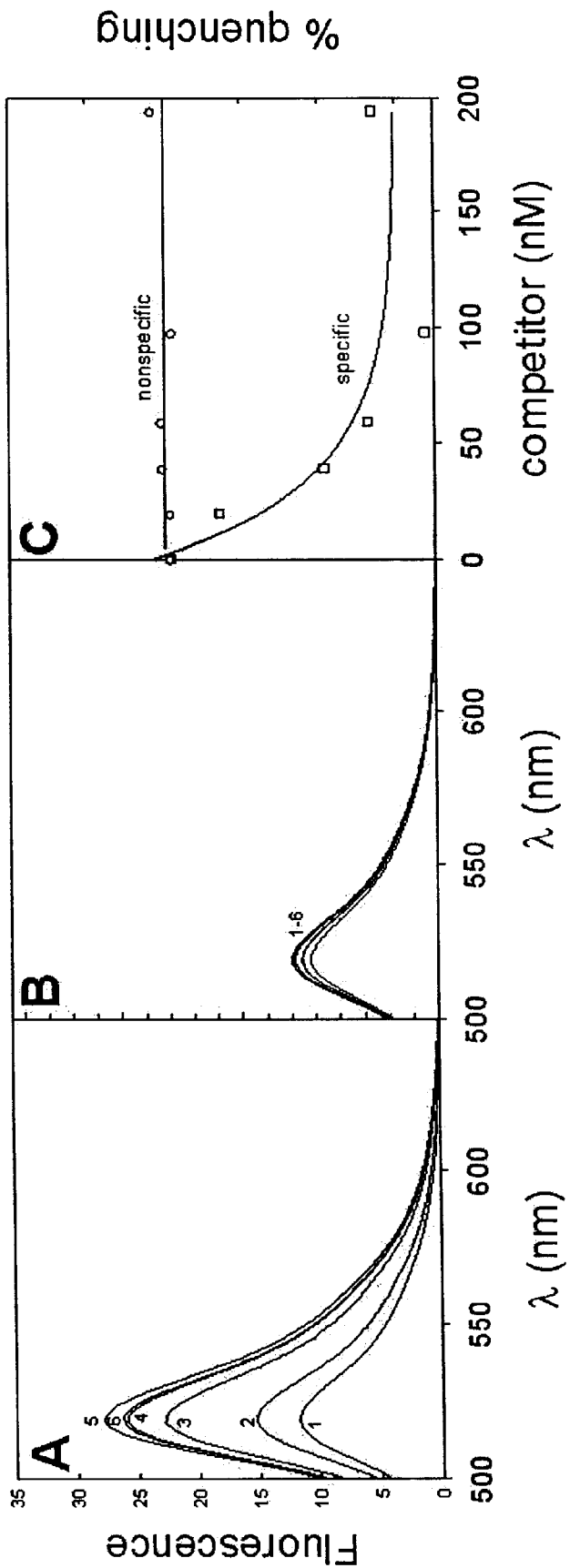
FIG. 5 depicts control experiments in which an unlabeled DNA fragment containing the CAP binding site blocks the change in fluorescence signal observed in the presence of CAP and a nonspecific DNA fragment does not affect a change in fluorescence signal.

FIG. 5 illustrates the experiments in which the effect of the addition of unlabeled DNA duplex on the assay was tested. Two 30 bp unlabeled DNA duplexes were prepared using the following oligonucleotides:

5'-CCTAAAATGTGATCTAGATCACATTTATTG-3' (SP1; SEQ ID NO:5)

5'-GCATCGGTCACTGCAGTCTCGACAGCTACG-3' (NSP1; SEQ ID NO:6)

To prepare 30 bp duplexes, SP1 and NSP1 oligonucleotides were hybridized with their respective complementary single-stranded oligonucleotides as described above for the CAP oligonucleotides. The SP1 DNA (SEQ ID NO:5) contains the consensus binding site for the CAP protein whereas the NSP1 DNA (SEQ ID NO:6) represents a random DNA sequence. First, the spectrum of 50 nM CAP2/CAP3 and 50 nM CAP2/CAP3 in the presence of 50 nM CAP in 50 mM Tris/HCl (pH 8.0), 50 mM NaCl, 1 mM EDTA, 0.1 mg/ml BSA, and 200 µM cAMP was recorded (curve 1, FIGS. 5A and 5B). The measurements were then repeated in the presence of increasing concentrations of either the SP1 duplex (FIG. 5A) or the NSP1 duplex (FIG. 5B). The following concentrations of the respective duplexes were used: 19.6 nM (curve 2), 39.1 nM (curve 3), 58.7 nM (curve 4), 97.6 nM (curve 5), and 194.2 nM (curve 6). The fluorescence quenching observed at each of these conditions is plotted in FIG. 5C. The DNA duplex containing the CAP binding site was able to efficiently block detection of CPA protein whereas the duplex containing the random sequence had no effect on CAP detection. Thus, the results shown in FIG. 5 provide additional evidence for the specificity of detection of CAP and also show that such competition assays may be used in the assessment of the relative binding affinities of proteins to various DNA molecules.

Figure 6:
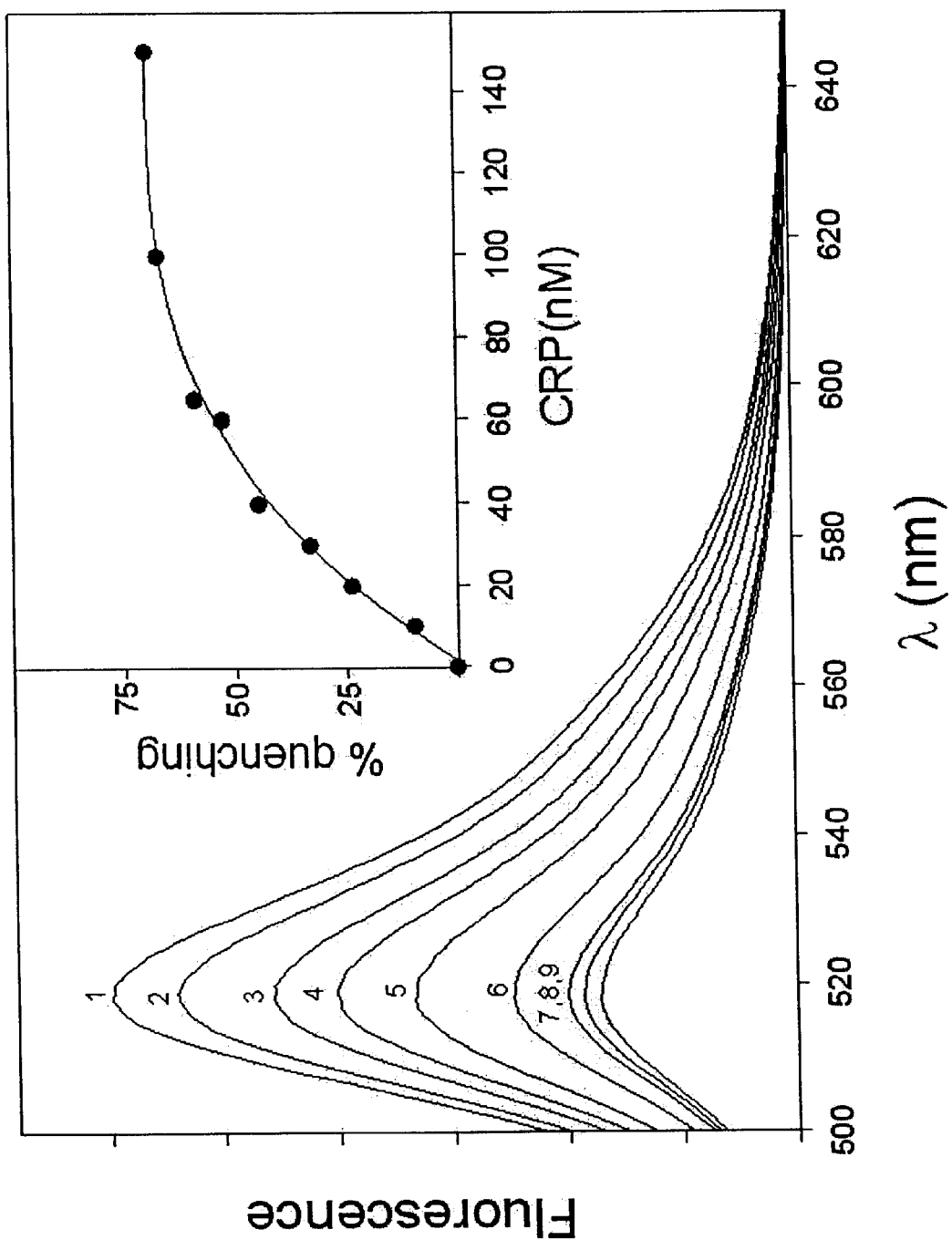
FIG. 6 depicts the dependence of the degree of change in fluorescence signal on the concentration of CAP protein.

FIG. 6 illustrates the change in fluorescence observed upon addition of increasing amounts of CAP protein in the assay. The experiments were performed under the same conditions as those for the experiment described above and in FIG. 4. Fluorescence quenching increased proportionally with the increase of CAP concentration until a saturation of the signal occurred at ~150 nM protein. This result suggests that the assay may be used for the determination of DNA binding protein concentrations in samples.

Figure 7:
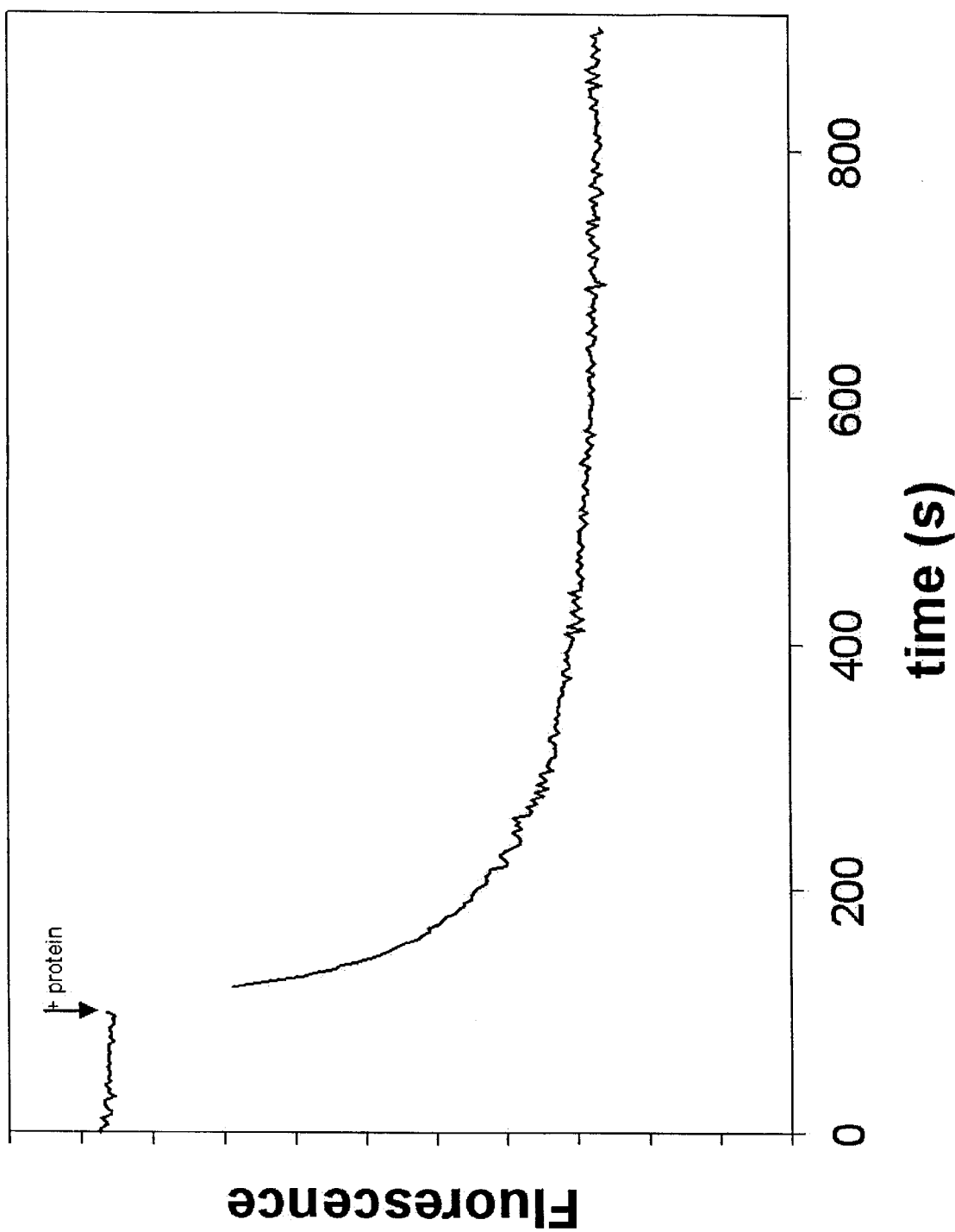
FIG. 7 shows the time dependence of fluorescence signal change in the presence of CAP.

The kinetics of CAP induced fluorescence quenching was also studied to determine the time required for completion of the assay (FIG. 7). In this experiment the fluorescence intensity of 50 nM CAP2/CAP3 and 50 nM CAP2/CAP3 was monitored as a function of time at 520 nm with the excitation wavelength set at 490 nm. At the time indicated by the arrow in FIG. 7, 100 nM CAP protein was added and monitoring of the fluorescence signal was resumed. According to the data, the reaction goes to completion in approximately 15 minutes suggesting that a 15–30 minute incubation time is sufficient for completion of this assay.

EXAMPLE 2

Demonstration of the Use of Fluorochromes with Different Emission Spectra and Different Modes of Fluorescence Signal Detection The following oligonucleotides, which have identical sequences to CAP2 and CAP4, respectively, were synthesized using standard phosphoramidate automated oligonucleotide synthesis, wherein X represents amino-dT:

5'-AGXAGATCACATTTTAGGCACC-3' (CAP5; SEQ ID NO:7)

5'-TCXACTTCACATTIATTGCGTT-3' (CAP6; SEQ ID NO:8)

Amino-Modifier C2 dT (Glen Research, Sterling, Va.) was incorporated into positions that are equivalent to the positions at which fluorescein-dT and dabcyl-dT has been used previously in CAP2 and CAP4 oligonucleotides, respectively. Amino-Modifier C2 dT contains a reactive aliphatic amino group that can be used to covalently attach any amino-reactive fluorescence probe. CAP5 (SEQ ID NO:7) and CAP6 (SEQ ID NO:8) oligonucleotides were modified with 7-diethylaminocoumarin-3-carboxylic acid, succinimidyl ester. This fluorophore is excited at 433 nm and the maximum emission occurs at 475 nm providing the possibility of testing the assay with different emission colors. To modify the fluorochrome, ~20 nmoles of the oligonucleotides were dissolved in 50 µl of 50 mM NaHCO$_3$ (pH 8.3) and 50 nmoles of dry 7-diethylaminocoumarin-3-carboxylic acid, succinimidyl ester (Molecular Probes, Eugene, Oreg.) were added. The reaction mixture was incubated overnight at room temperature. The excess uncoupled dye was removed on a G-25 spin column (Amersham Pharmacia Biotech, Piscataway, N.J.) and the labeled oligonucleotides were further purified by reverse phase chromatography as previously described. The fractions containing the fluorochrome-labeled oligonucleotides were dried in Vacuum centrifuge concentrator and were dissolved in 50 µl of water. The concentrations of the stock solutions of the oligonucleotides were determined by recording the UV-VIS absorption spectrum of a small aliquot of the stock solution diluted to 400µl. The 7-diethylaminocoumarin-3-carboxylic acid labeled CAP5 oligonucleotide was hybridized with CAP3 oligonucleotide to generate the CAP5/CAP3 duplex. The 7-diethylaminocoumarin-3-carboxylic acid labeled CAP6 oligonucleotide was hybridized with CAP1 oligonucleotide to generate the CAP6/CAP1 duplex. For the hybridization, the appropriate oligonucleotides were mixed at 10 µM concentration in 100 µl of 50 mM Tris/HCl (pH 8.0), 100 mM NaCl, 1 mM EDTA, heated for 1 min at 95° C. and then cooled to 25° C. for 1 hr.

Figure 8:
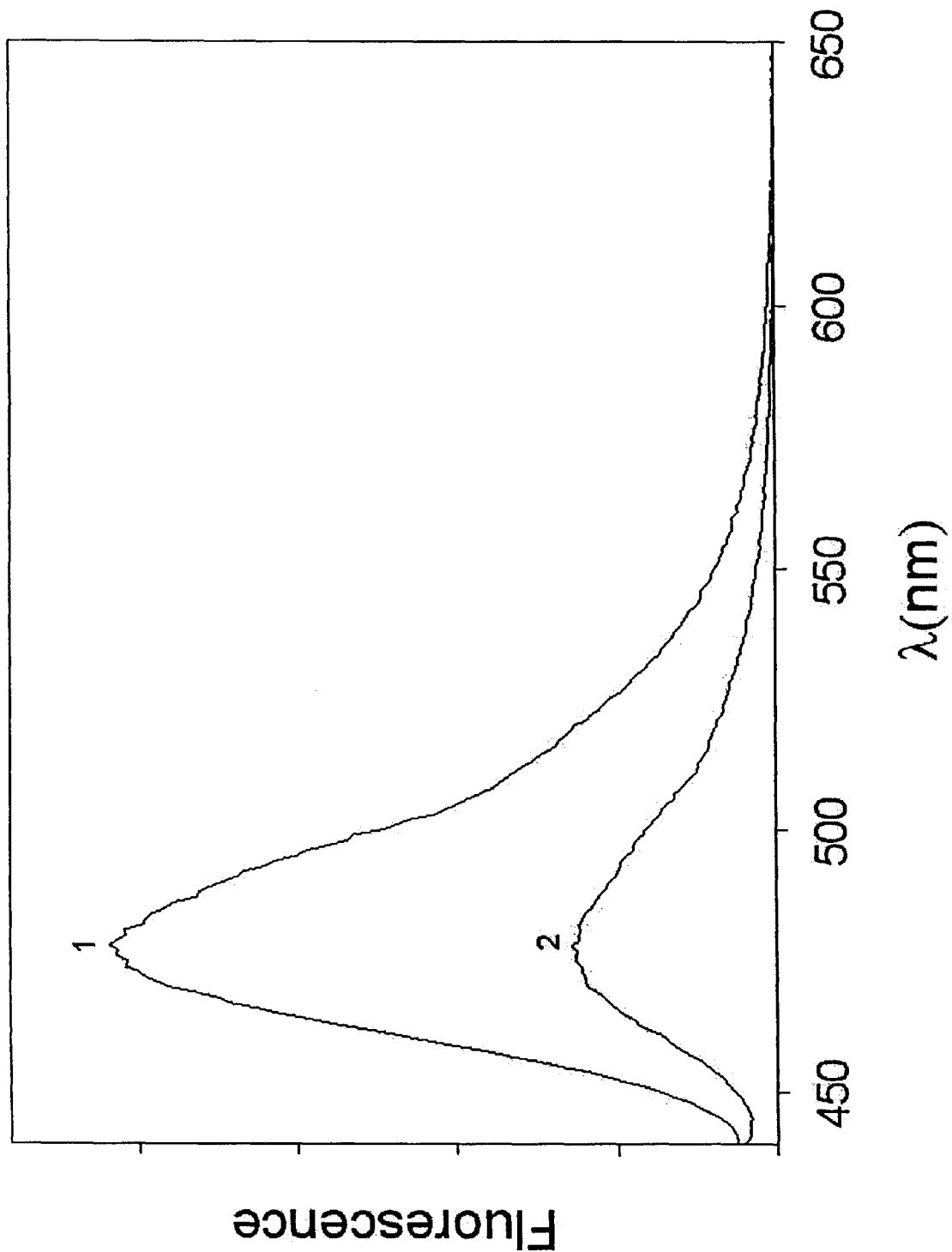
FIG. 8 illustrates the use of 7-diethylaminocoumarin-3-carboxylic acid for the detection of CAP protein. Curve 1 represents no CAP present. Curve 2 represents the presence of 100 nM CAP.

In the first experiment (FIG. 8), the pair of CAP5/CAP3 and CAP4/CAP1 nucleic acid duplexes were tested in the CAP assay. In this format, the 7-diethylaminocoumarin-3-carboxylic acid label present in the CAP5/CAP3 duplex functions as the fluorescence donor and the dabcyl label present in the CAP4/CAP1 duplex functions as a fluorescence acceptor. The experiment was performed at 25° C. in 50 mM Tris/HCl (pH 8.0), 100 mM NaCl, 1 mM EDTA, 0.1 mg/ml BSA, and 200 µM cAMP. Curve 1 of FIG. 8 shows the fluorescence spectrum of a 50 nM solution of CAP5/CAP3 plus CAP4/CAP1 in the absence of CAP protein. Addition of 100 nM of CAP resulted in the dramatic quenching (~70%) of the fluorescence signal as expected (FIG. 8, curve 2).

Figure 9:
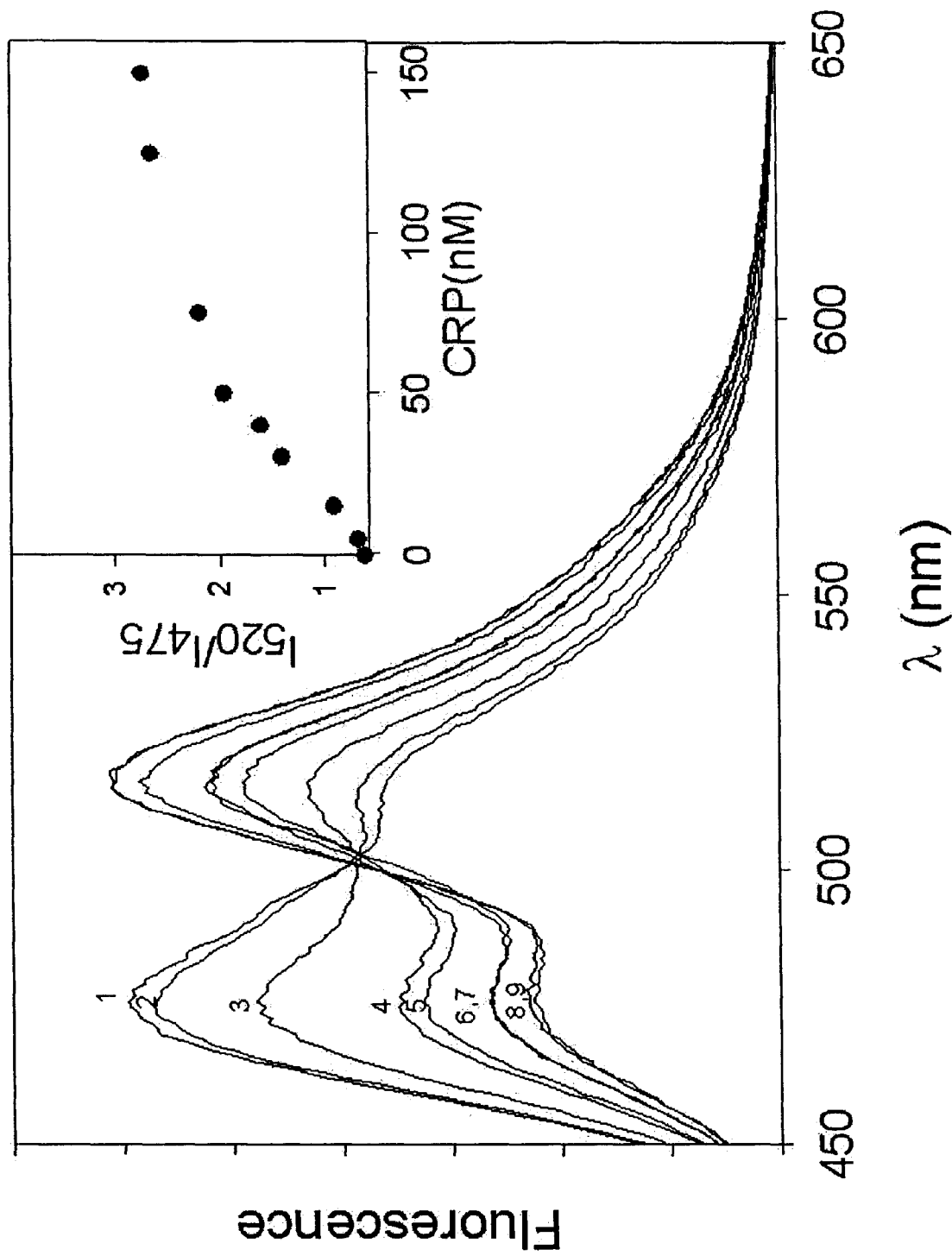
FIG. 9 depicts the use of the ratio of fluorescence at different wavelengths for the detection of CAP protein. Curves 1–9 represent increasing amounts of CAP, from 0 to 150 nM, respectively.

In a second experiment (FIG. 9), the pair of CAP6/CAP1 and CAP2/CAP3 nucleic acid duplexes were tested for the performance in CAP assay. In this assay format, the 7-diethylaminocoumarin-3-carboxylic acid present in the CAP6/CAP1 duplex functioned as a fluorescence donor and the fluorescein present in the CAP2/CAP3 duplex functioned as an acceptor. In this case, both the donor as well as the acceptor are fluorescent. The experiment was performed at 25° C. in 50 mM Tris/HCl (pH 8.0), 100 mM NaCl, 1 mM EDTA, 0.1 mg/ml BSA, and 200 µM cAMP. Curve 1 of FIG. 9 shows the fluorescence spectrum of 50 nM solution of CAP6/CAP1 plus CAP2/CAP3. The excitation wavelength was at 433 nm, therefore the major emission peak was observed at 475 nm, which is the emission maximum for 7-diethylaminocoumarin-3-carboxylic acid. The shoulder observed at about 520 nm is due to the residual emission of fluorescein, which is also to a small extent excited at 433 nm. Upon addition of varying amounts of CAP in a range from 0 to 150 nM (curves 2–9), a pronounced quenching of the peak at 475 nm and a pronounced enhancement of the peak at 520 nm is observed. Recall that the emission maximum of fluorescein is 520 nm. This data shows that the detection of the CAP protein, or any cognate DNA binding protein, may be accomplished either by quenching of fluorescence at 475 nm or by enhancement of fluorescence at 520 nm. Also, as shown in the inset of FIG. 9, the ratio between the fluorescence intensities at 520 nm and 475 nm may be used to determine the concentration of DNA binding proteins. This ratiometric mode of signal detection could be particularly useful since it would be less prone to trivial errors (such as pipetting errors, general quenching by some unrelated compounds present in the assayed sample). Taken together, the data presented in this example show that the assay method described in this invention provides a great flexibility in terms of the nature of the fluorescent probe used, the emission spectrum of the probe, and the mode of fluorescence signal detection.

EXAMPLE 3

The Detection of Analytes, for Example cAMP

The activity of many DNA binding proteins is regulated by small molecules, other proteins or cellular events (e.g., phosphorylation). Hence, it is envisioned that the present invention may be used to identify or detect these regulatory molecules or regulatory cellular events.

CAP protein binds both CAMP and cGMP with micromolar affinity (Takahashi, M., Blazy, B., and Baudras, A. Biochemistry 19, 5124–30). Thus, CAP protein, by itself, is a poor reagent for specifically detecting CAMP. However, the high affinity of CAP for its cognate DNA binding sequence is selectively dependent on CAMP, but not cGMP. Since only cAMP is thermodynamically linked to sequence-specific DNA binding, in the presence of DNA containing a CAP binding site, the affinity of CAP for cAMP is increased about 1000-fold, whereas the affinity for cGMP remains unchanged. Thus, in the presence of DNA containing a CAP binding site, CAP becomes a sensitive and selective sensor of cAMP.

Figure 10:
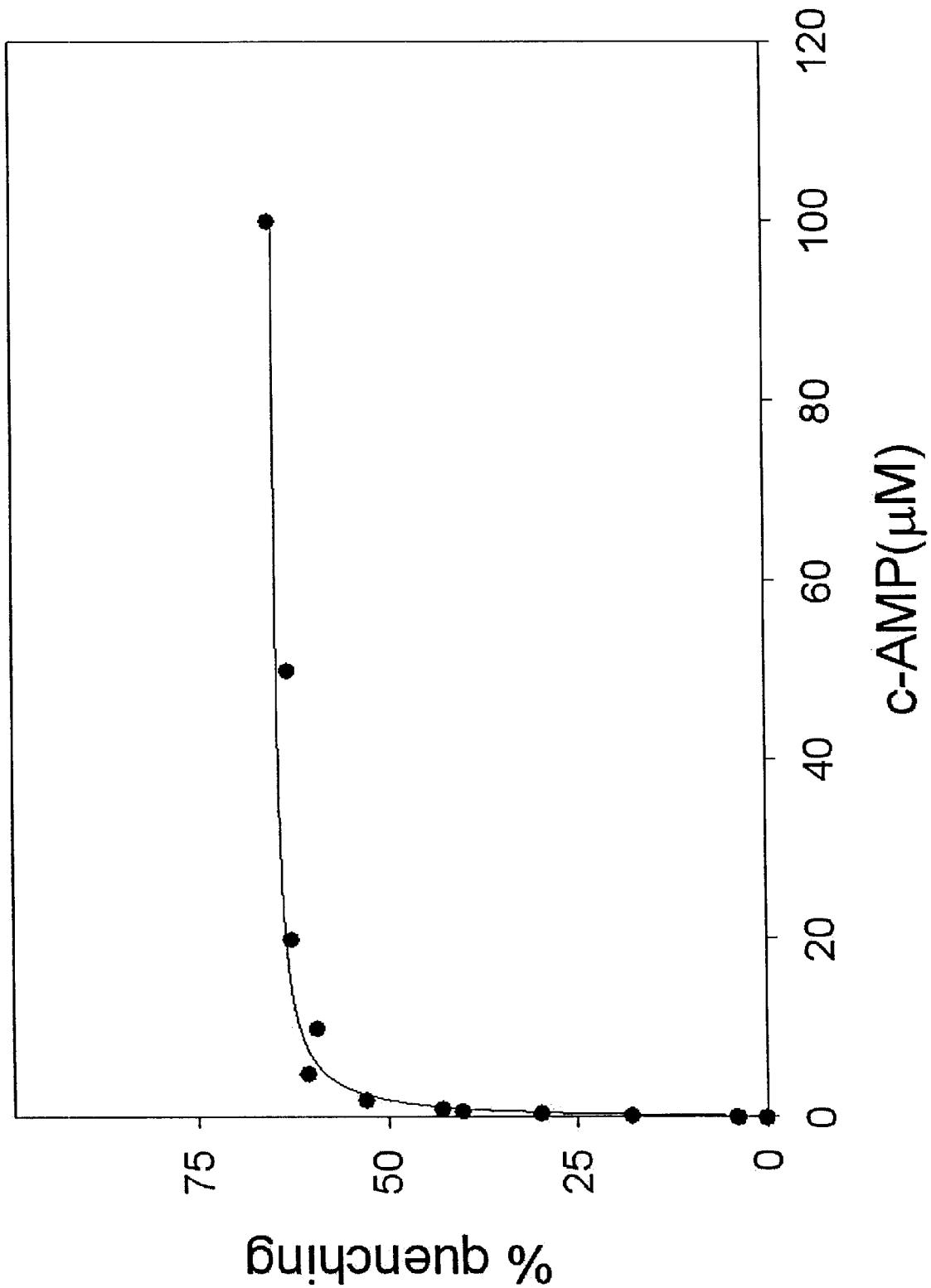
FIG. 10 depicts the effect of the analyte CAMP upon CAP binding to the CAP1/CAP4 and CAP2/CAP3 DNA duplex. No binding occurs in the absence of cAMP.

As already demonstrated in FIG. 4C, in the absence of cAMP, CAP protein does not produce a change in fluorescence signal intensity. To demonstrate the detection of cAMP using CAP the assay, the fluorescence intensity of 50 nM solution of CAP1/CAP4 plus CAP2/CAP3 in 50 mM Tris/HCl (pH 8.0), 50 mM NaCl, 1 mM EDTA, 0.1 mg/ml BSA containing 75 nM CAP was measured at different concentrations of CAMP ranging form 0 to 100 mM. FIG. 10 shows that, as expected, a fluorescence quenching proportional to the concentration of CAMP was observed with a saturation of the signal occurring a approximately 5 µM CAMP. Thus, the present invention may be used as a sensitive detector for CAMP or any other agent or event that potentiates DNA binding.

The flexibility of the assay design, which is a particular strength of the present invention, allows for the optimization of the assay in terms of sensitivity, color of fluorescence emission, and/or mode of fluorescence signal detection. While this example illustrates the use of the invention to detect cAMP, it is envisioned that the invention is not limited to CAMP detection. Any molecule, whose presence could be linked to changes in the affinity for DNA by a DNA binding protein, may be detected using this invention. More generally, any process which affects the affinity of a DNA binding protein to a DNA may also be assayed using this invention.

EXAMPLE 4

Assay Variant with the DNA Linked by a Long Flexible Linker

Figure 11:
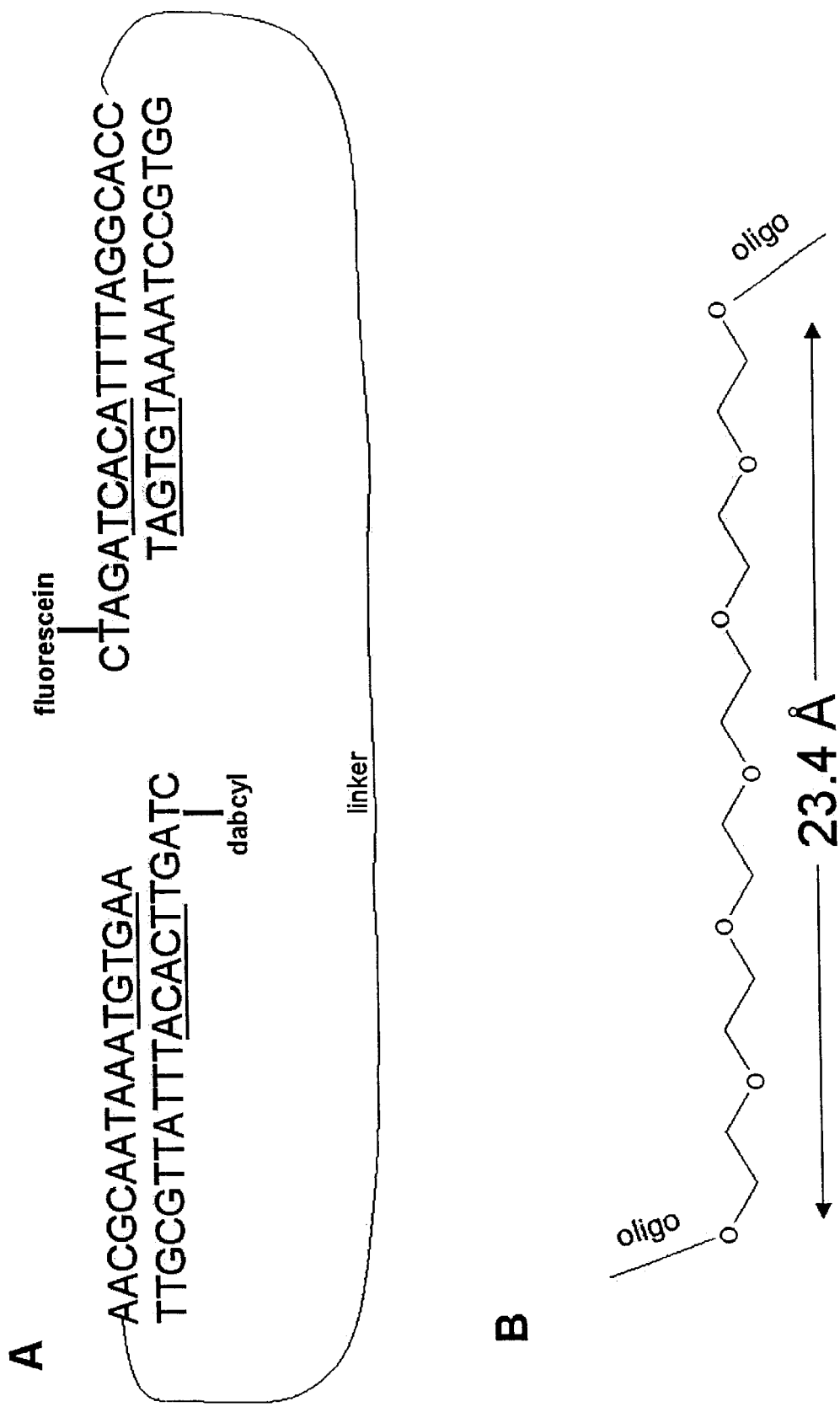
FIG. 11 illustrates the design of an assay in which the two DNA molecules are covalently linked by a long flexible linker to remove dependency of the assay on DNA concentration and to reduce the time necessary to perform the assay. Panel B depicts one unit of a spacer-18-phosphoramidate moiety.

The properties of the assay illustrated in FIG. 1 depend upon the total concentration of the nucleic acid fragments. By covalently linking the two DNA duplexes—i.e., the components of the assay—by a long flexible linker, the assay becomes independent of DNA concentration, within a range of detectability of fluorescence signal and within a range of concentration required for efficient protein binding. FIG. 11 illustrates the design this variant of the assay for CAP detection. The nucleic acid components of the assay were covalently linked during oligonucleotide synthesis by introducing 12 moieties of the Spacer 18 phosphoramidate (Glen Research, Sterling, Va.), the structure of which is shown in FIG. 11B. The addition of 12 units of Spacer 18 results in a distance of ~270 Å between the linked oligonucleotides. The following oligonucleotides were prepared (F =dT-fluorescein, D=dT-dabcyl, X=Spacer 18):

CFA GAT CAC ATT TTA GGC ACC XXX XXX XXX XXX AAC GCA ATA AAT GTG AT (CAP7; SEQ ID NO:9)

CDA GAT CAC ATT TAT TGC GTT (CAP8; SEQ ID NO:10)

GGT GCC TAA AAT GTG AT (CAP9; SEQ ID NO:11)

The oligonucleotides were purified using reverse phase chromatography on a RPC column (Amersham Pharmacia Biotech, Piscataway, N.J.) as previously described (Heyduk, E., and Heyduk, T. Anal. Biochem. 248, 216–227, 1997). The fractions containing the oligonucleotides were dried in a Vacuum centrifuge concentrator and then dissolved in 50 µl of water. The concentration of the stock solutions of oligonucleotides was determined by recording the UV-VIS absorption spectrum of a small aliquot of the stock solution diluted to 400 µl. To generate the CAP7/CAP8/CAP9 duplex (FIG. 11A), the CAP7, CAP8, and CAP9 oligonucleotides (SEQ ID NOS:9, 10 and 11, respectively) were mixed at 10 µM concentration in 100 µl of 50 mM Tris/HCl (pH 8.0), 100 mM NaCl, 1 mM EDTA, heated for 1 min at 95° C. and then cooled to 25° C. in 1 hr.

An additional advantage of this embodiment of the invention is that the incubation time necessary for the development of the signal is shortened, because when the nucleic acid components are linked, as shown in FIG. 11A, the rate of association reaction between the nucleic acid components is increased due to the relatively close proximity of each component. This variation of the invention is preferred if the attachment of the nucleic acid components to a solid support is desired. It is envisioned that a reactive amino group may be included in the linker, which would be used for the attachment of the entire nucleic acid construct to the solid support.

Figure 12:
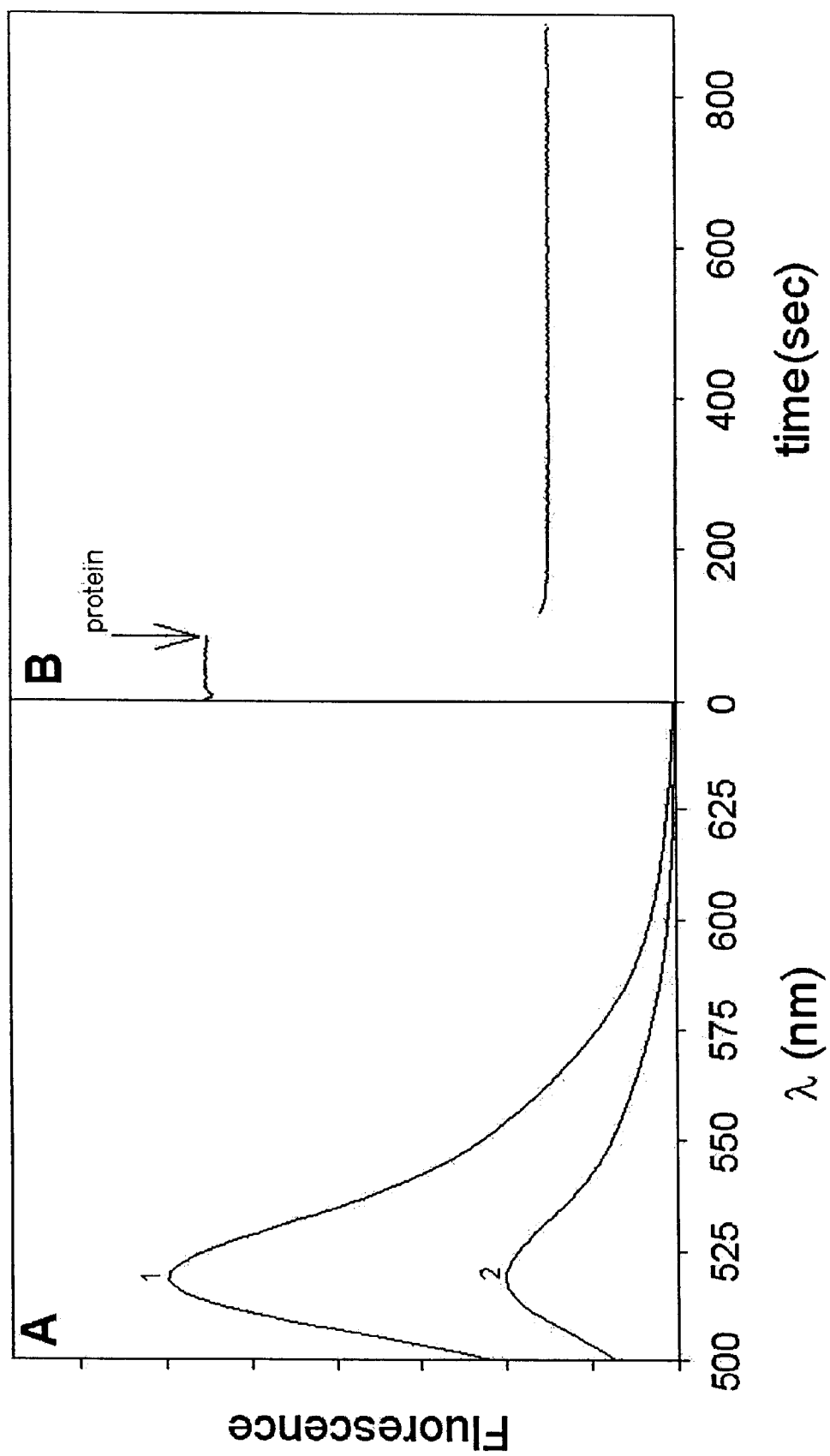
FIG. 12 depicts the fluorescence signal change observed in the presence of CAP using the covalently linked design depicted in FIG. 11. Panel B depicts the response time of quenching using the flexible-linker construct.

FIG. 12 illustrates the enhanced performance of the variation of the invention depicted in FIG. 11. Curve 1 of FIG. 12A shows the spectrum of 50 nM of the CAP7/CAP8/CAP9 construct in 50 mM Tris/HCl (pH 8.0), 50 mM NaCl, 1 mM EDTA, 0.1 mg/ml BSA, and 200 µM cAMP. The addition of 75 nM CAP protein resulted in ~70% quenching of the fluorescence signal, demonstrating that a DNA binding protein may be readily detected by this assay format. The kinetics of CAP induced fluorescence quenching was also studied to determine the incubation time necessary for the completion of the assay (FIG. 12B). In this experiment, the fluorescence intensity of 50 nM of the CAP7/CAP8/CAP9 construct was monitored as a function of time at 520 nm with the excitation wavelength set at 490 nm. At the time indicated by the arrow in FIG. 12B, 75 nM CAP protein was added and the monitoring of the fluorescence signal was resumed. The reaction was essentially completed within the time it took to add the CAP protein (within approximately 20 sec). Thus, the linking of the nucleic acid components resulted in a dramatic decrease in the time necessary for a change in the fluorescence signal to occur.

EXAMPLE 5

The Detection of the Lac Repressor Protein (LacR)

To illustrate the universal capability of the invention to detect, identify or quantify any DNA binding protein, the following oligonucleotides, which comprise Lac repressor binding elements, were synthesized (F=dT-fluorescein, D=dT-dabcyl):

GGTGTGTGGMTTGTGA (LAC1; SEQ ID NO:12)

GCGFATAACAATTTCACACAGG (LAC2; SEQ ID NO:13)

CTTGTGTGAAATTGTT (LAC3; SEQ ID NO:14)

ADACGCTCACAATTCCACACACC (LAC4; SEQ ID NO:15)

Figure 13:
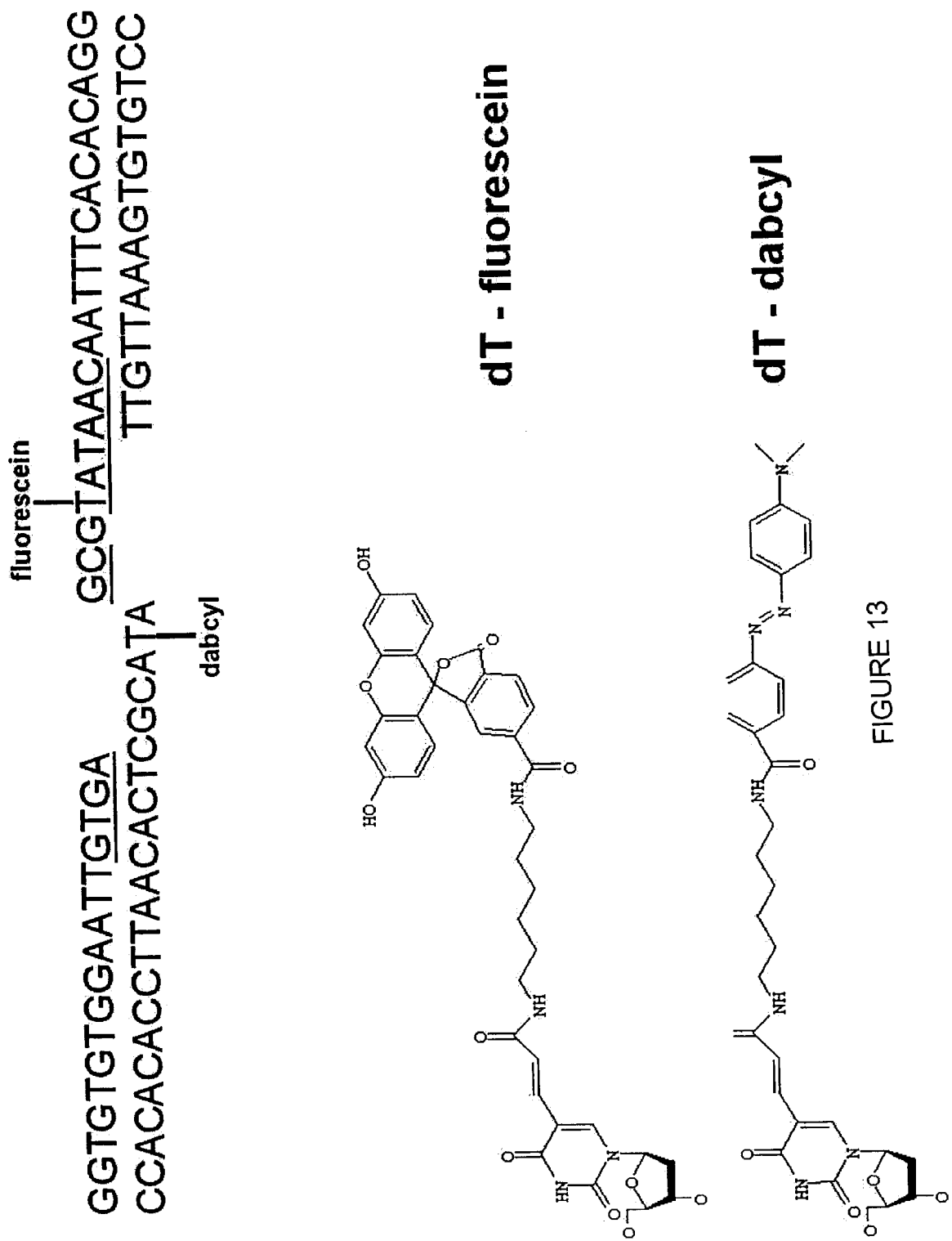
FIG. 13 depicts the fluorochrome-labeled oligonucleotides of SEQ ID NOS:12–15 for the detection of the LacR protein.

The oligonucleotides were purified using reverse phase chromatography on RPC column (Amersham Pharmacia Biotech, Piscataway, N.J.) as previously described (Heyduk, E., and Heyduk, T. *Anal. Biochem.* 248, 216–227, 1997). The fractions containing the oligonucleotides were dried in Vacuum centrifuge concentrator and were dissolved in 50 µl of water. The concentration of the stock solutions of oligonucleotides was determined by recording the UV-VIS absorption spectrum of a small aliquot of the stock solution diluted to 400 µl. The LAC1 oligonucleotide (SEQ ID NO:12) was hybridized with the LAC4 oligonucleotide (SEQ ID NO:15) to generate the LAC1/LAC4 construct and the LAC2 oligonucleotide (SEQ ID NO:13) was hybridized with the LAC3 oligonucleotide (SEQ ID NO:14) to generate the LAC2/LAC3 construct. For the hybridization, the appropriate oligonucleotides were mixed at 10 µM concentration in 100 µl of 50 mM Tris/HCl (pH 8.0), 100 mM NaCl, 1 mM EDTA, heated for 1 min at 95° C. and then cooled to 25° C. for 1 hr. All subsequent fluorescence measurements were performed at 25° C. in 50 mM Tris/HCl (pH 8.0), 100 mM NaCl, 1 mM EDTA, and 0.1 mg/ml BSA. The double stranded nucleic acid constructs obtained upon hybridization are illustrated in FIG. 13. The duplexes contain a LacR binding site (underlined sequence) derived from the Lac operon sequence split between each of the two double stranded constructs.

Figure 14:
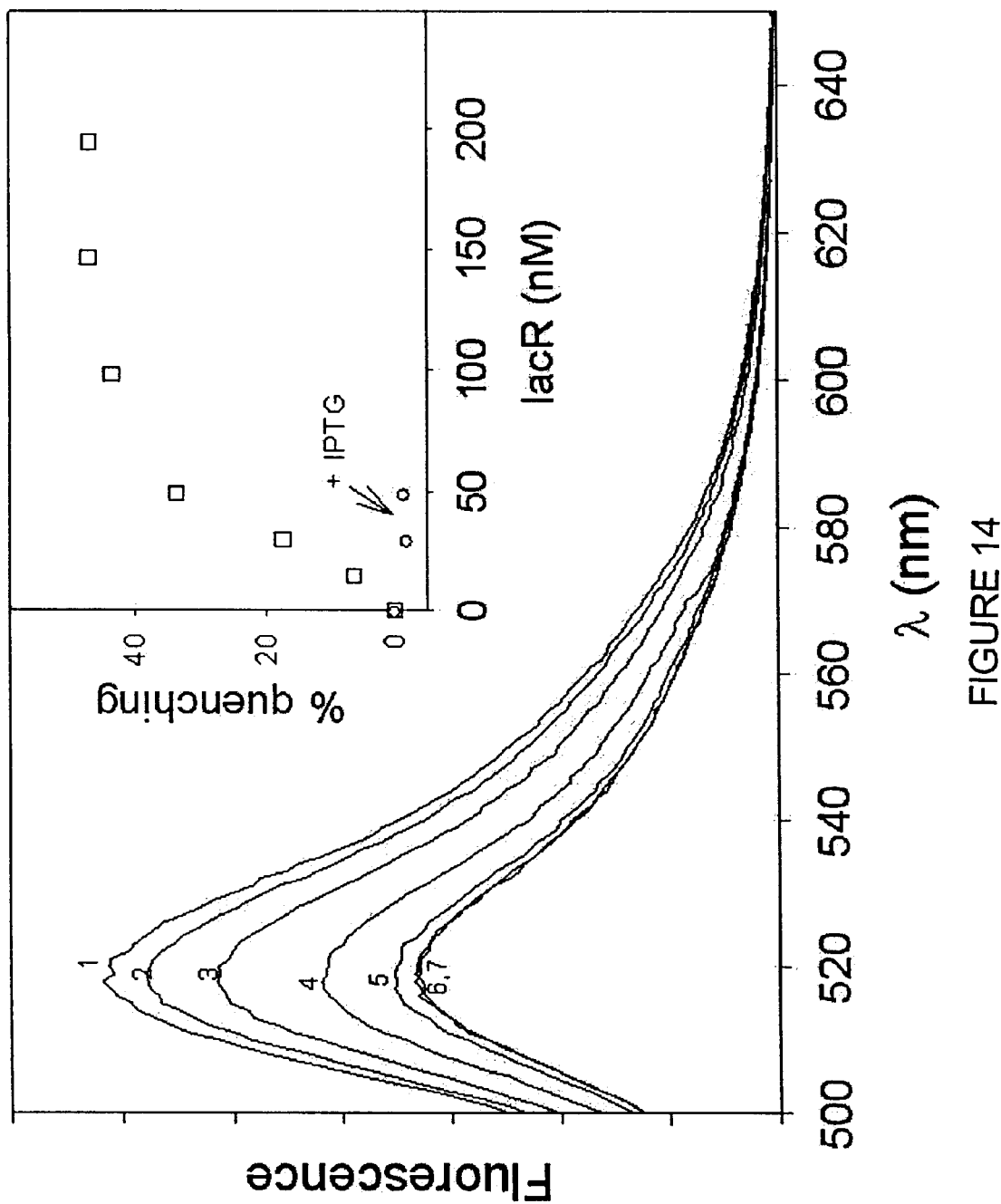
FIG. 14 depicts fluorescent quenching due to the binding of LacR protein to the cognate DNA sequences. Curves 1–7 represent increasing amounts of LacR protein, from 0 to 200 nM, respectively.

The fluorescence spectra of 50 nM of LAC1/LAC4 plus LAC2/LAC3 were recorded in the absence of LacR (FIG. 14, curve 1) and in the presence of varying amounts of LacR in a range from 0–200 nM (FIG. 14, curves 2–7). Fluorescence signal quenching was proportional to the amount of LacR added to the reaction mixture, with saturation occurring at approximately 150 nM of LacR (FIG. 14, inset). Thr specificity of LacR detection was confirmed by adding 5 mM IPTG to the assay mixture, which selectively binds to LacR and reduces its DNA binding activity.

EXAMPLE 6

The Detection of the Trp Repressor Protein (TrpR)

To further illustrate the universal capability of the present invention to detect any and all DNA binding proteins, the following oligonucleotides, which comprise a Trp repressor binding element, were synthesized (F=dT-fluorescein, D=dT-dabcyl):

GAGATCTATCGAACTA (TRP1; SEQ ID NO:16)

GFA AAC TAG TAC GAA ACT AGA G (TRP2; SEQ ID NO:17)

CTC TAG TTT CGT ACT A (TRP3; SEQ ID NO:18)

GDT TAC TAG TTC GAT AGA TCT C (TRP4; SEQ ID NO:19)

Figure 15:
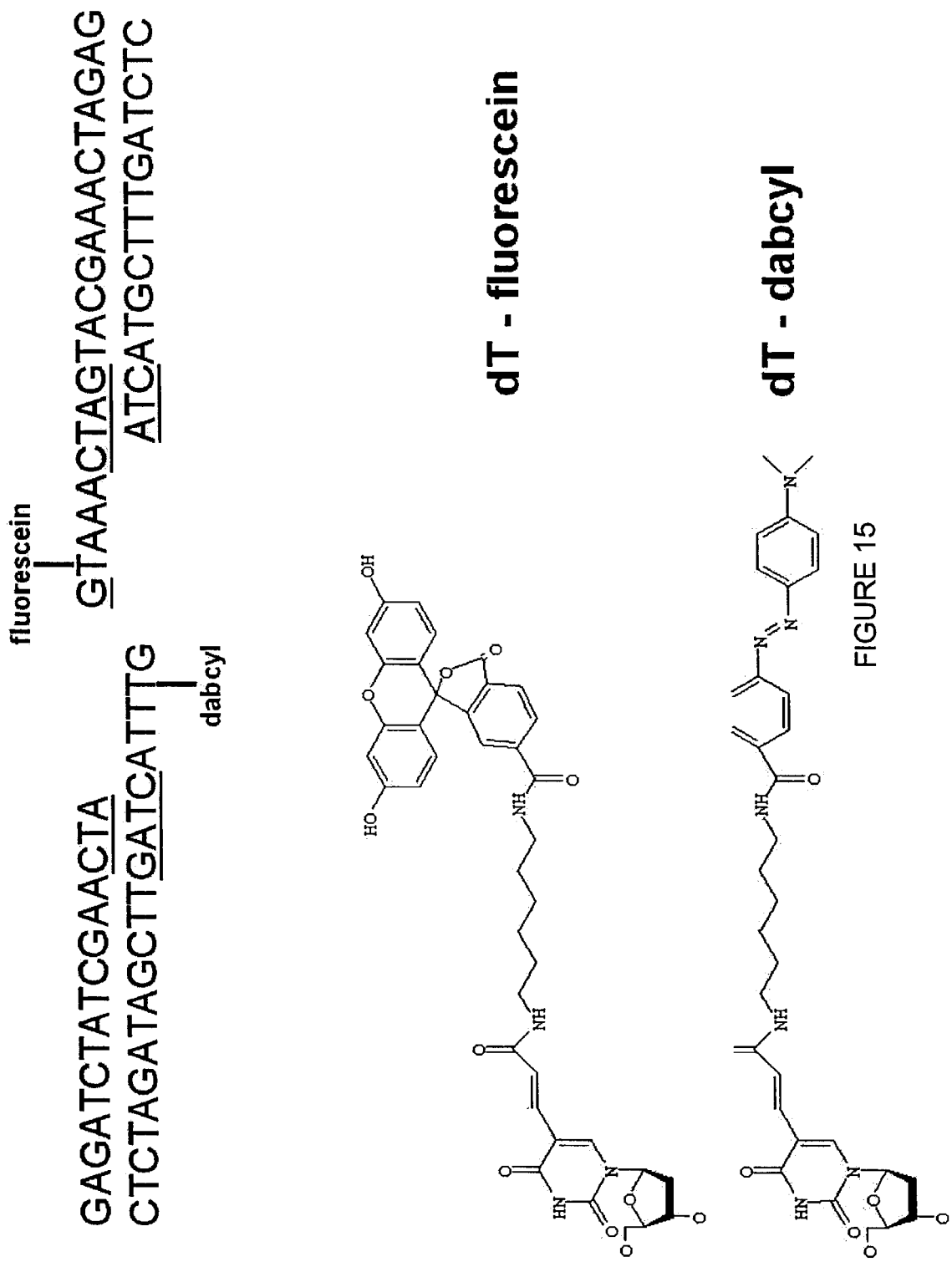
FIG. 15 depicts the nucleic acid duplexes of SEQ ID NO:16–19 containing portions of the TrpR protein binding sites.

The oligonucleotides were purified using reverse phase chromatography on RPC column (Amersham Pharmacia Biotech, Piscataway, N.J.) as previously described (Heyduk, E., and Heyduk, T. *Anal. Biochem.* 248, 216–227, 1997). The fractions containing the oligonucleotides were dried in Vacuum centrifuge concentrator and were dissolved in 50 µl of water. The concentration of the stock solutions of oligonucleotides was determined by recording the UV-VIS absorption spectrum of a small aliquot of the stock solution diluted to 400 µl. The TRP1 oligonucleotide (SEQ ID NO:16) was hybridized with the TRP4 oligonucleotide (SEQ ID NO:19) to generate the TRP1/TRP4 construct and the TRP2 oligonucleotide (SEQ ID NO:17) was hybridized with the TRP3 oligonucleotide (SEQ ID NO:18) to generate the TRP2/TRP3 construct. For the hybridization, the appropriate oligonucleotides were mixed at 10 µM concentration in 100 µl of 50 mM Tris/HCl (pH 8.0), 100 mM NaCl, 1 mM EDTA, heated for 1 min at 95° C. and then cooled to 25° C. for 1 hr. All subsequent fluorescence measurements were performed at 15° C. in 10 mM potassium phosphate (pH 7.6), 50 mM NaCl, 0.1 mM EDTA, 4mM tryptophan, 10% glycerol, 0.01% sodium azide and 1.0 mg/ml BSA. The double stranded nucleic acid constructs obtained upon hybridization are illustrated in FIG. 15. The duplexes contain a TrpR binding site (underlined sequence) split between each of the two double stranded constructs.

Figure 16:
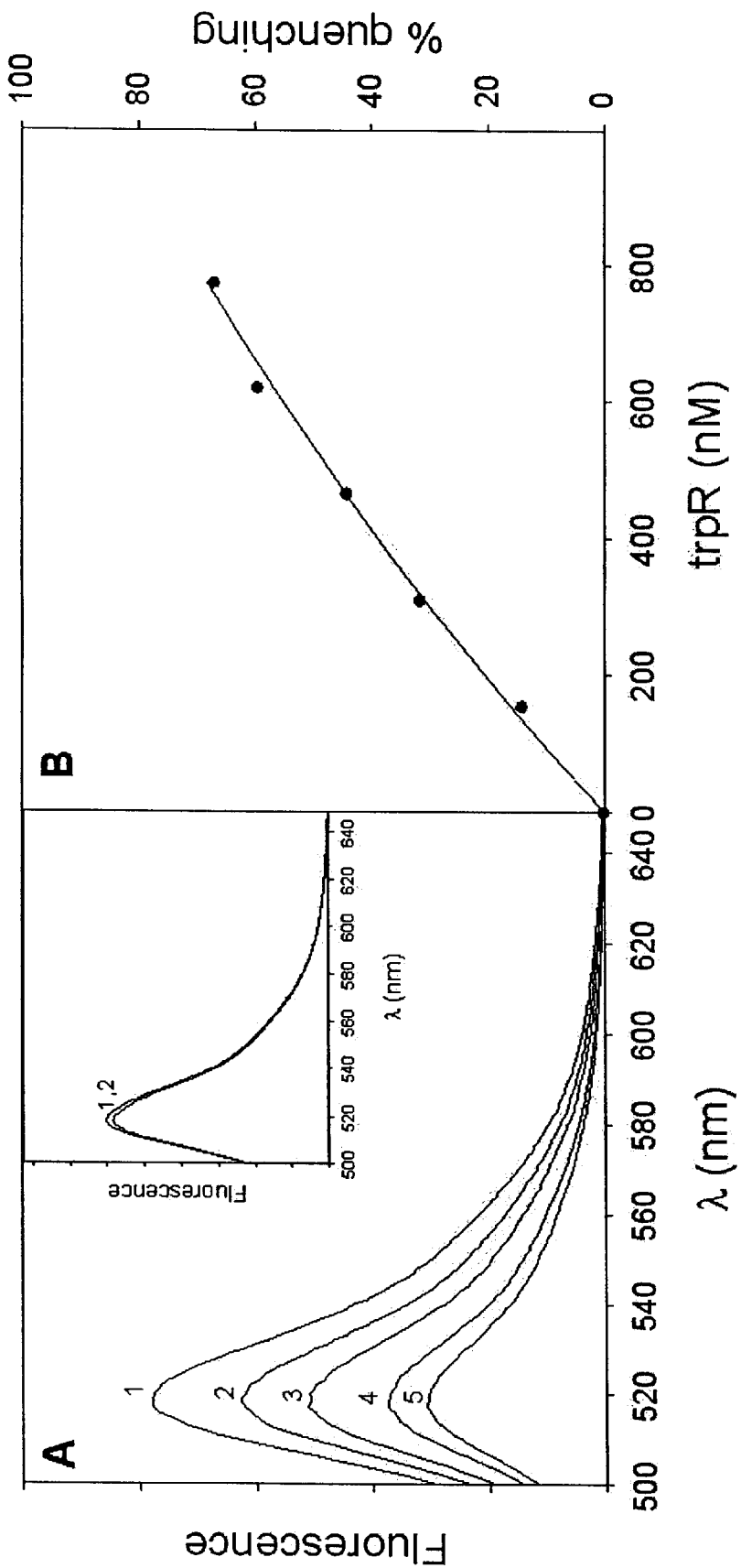
FIG. 16 depicts fluorescent quenching due to the binding of TrpR protein to the cognate DNA sequences. Curves 1–5 represent increasing amounts of TrpR protein, from 0 to 800 nM, respectively.

The fluorescence spectra of 250 nM TRP1/TRP4 and 300 nM TRP2/TRP3 were recorded in the absence of TrpR (FIG. 16A, curve 1) and in the presence of varying amounts of TrpR in a range from 0–800 nM (FIG. 16A, curves 2–5). ). Fluorescence signal quenching was proportional to the amount of TrpR added to the reaction mixture, with saturation occurring at approximately 150 nM of LacR (FIG. 16B). The specificity of TrpR detection was confirmed by the addition of TrpR to a reaction mixture containing the nucleic acid components used for detecting LacR protein (FIG. 16A, inset, curves 1 and 2).

EXAMPLE 7

The Simultaneous Detection of Two Proteins Using a Two-color Detection Protocol

The compatibility of the assays described in the instant invention with a variety of fluorescence probes emitting at different wavelengths allows for the designing of variations in which two or more proteins may be detected simultaneously. Nucleic acid constructs specific for each of the proteins to be detected may be labeled with probes that emit light at different wavelengths. In this example, the reaction mixture contained nucleic acid constructs labeled with 7-diethylaminocoumarin-3-carboxylic acid for detecting CAP protein (described in EXAMPLE 2) and nucleic acid constructs labeled with fluorescein for detecting TrpR protein (described in EXAMPLE 6). Specifically, 100 nM CAP5/CAP3, 120 nM CAP1/CAP4, 100 nM TRP2/TRP3, and 120 nM TRP1/TRP4 duplexes were present in the reaction mixture.

Figure 17:
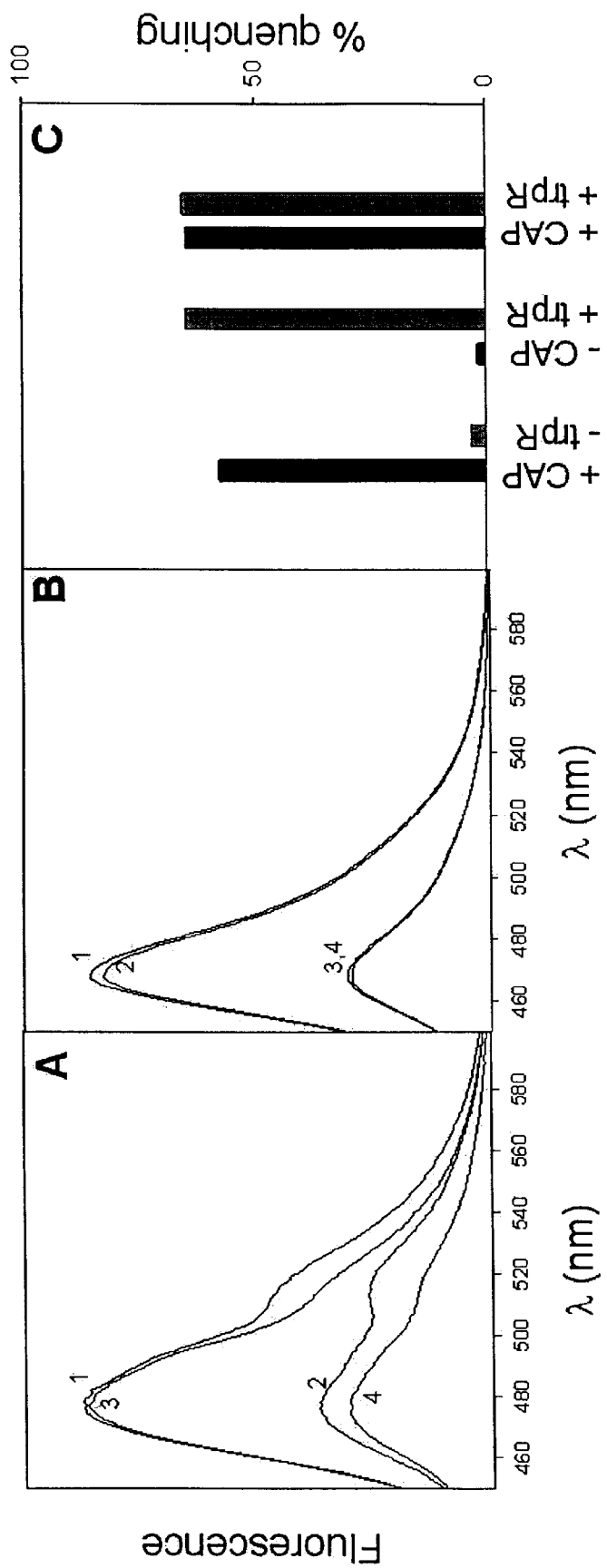
FIG. 17 depicts the simultaneous two-color detection of two proteins, CAP and TrpR. Panel A depicts the fluorescence spectra obtained at 433 nm excitation wavelength and panel B depicts the fluorescence spectra obtained at 490 nm excitation wavelength. Curves 1 are in the absence of both proteins, curves 2 in the presence of CAP only, curves 3 in the presence of TrpR only and curves 4 in the presence of both CAP and TrpR. Panel C summarizes the results from panels A and B.

FIG. 17 shows the results of the experiment illustrating this capability. All measurements were performed at 15° C. in 10 mM potassium phosphate (pH 7.6), 50 mM NaCl, 0.1 mM EDTA, 4mM tryptophan, 200 µM cAMP, 10% glycerol, 0.01% sodium azide and 1.0 mg/ml BSA. The fluorescence spectra with the excitation at 433 nm (excitation of 7-diethylaminocoumarin-3-carboxylic acid, FIG. 17A) and with the excitation at 490 nm (excitation of fluorescein, FIG. 17B) were recorded in the absence of the proteins (curves 1), in the presence of CAP only (curves 2), in the presence of TrpR only (curves 3), and in the presence of both CAP and TrpR (curves 4). In the presence of only CAP there was no change in the fluorescein signal (FIG. 17B, curve 2) whereas about 60% quenching of the 7-diethylaminocoumarin-3-carboxylic acid signal was observed (FIG. 17A, curve 2). In the presence of only TrpR there was no change in the 7-diethylaminocoumarin-3-carboxylic acid signal (FIG. 17A, curve 3) whereas about 60% quenching of the fluorescein signal was observed (FIG. 17B, curve 3). Finally, when both CAP and TrpR were present the quenching of both emission spectra was observed (FIGS. 17A & B, curves 4). FIG. 17C summarizes these results in a form of a bar plot in which the dark bars correspond to the quenching observed at the color for CAP detection, and shaded bars correspond to the quenching at the color for detection of TrpR. It is evident from the data presented in this example that simultaneous multi-color detection of two or more analytes may also be achieved using the assay described in the present invention.

EXAMPLE 8

The Detection of p53 Protein

Mutations in the p53 protein are crucial to the development of many tumors, wherein a majority of tumors contain mutations in this protein (Ko, L. L., andPrives, C. *Genes Dev.* 10, 1054–1072, 1996). Furthermore, tumors that lack functional p53 protein are recalcitrant to radiation therapy. The p53 protein binds double-stranded DNA in a sequence specific manner and its DNA binding activity is essential for its function. The majority of mutant p53s isolated from human tumors are deficient in DNA binding activity. Therefore, functional assays directed to the presence of and specific activity of p53 will provide an important diagnostic tool to be used in cancer identification and treatment.

To illustrate the capability of the assay for the detection of p53 protein, the following oligonucleotides, which comprise a cognate p53 binding element, were synthesized (F=dT-fluorescein, D=dT-dabcyl):

GCA TCG GTC ACA GAC A (P1; SEQ ID NO:20)

TGC CFA GAC ATG CCT TGC AGT CTC GA (P2; SEQ ID NO:21)

TCG AGA CTG CAA GGC A (P3; SEQ ID NO:22)

TGT CDA GGC ATG TCT GTG ACC GAT GC (P4; SEQ ID NO:23)

Figure 18:
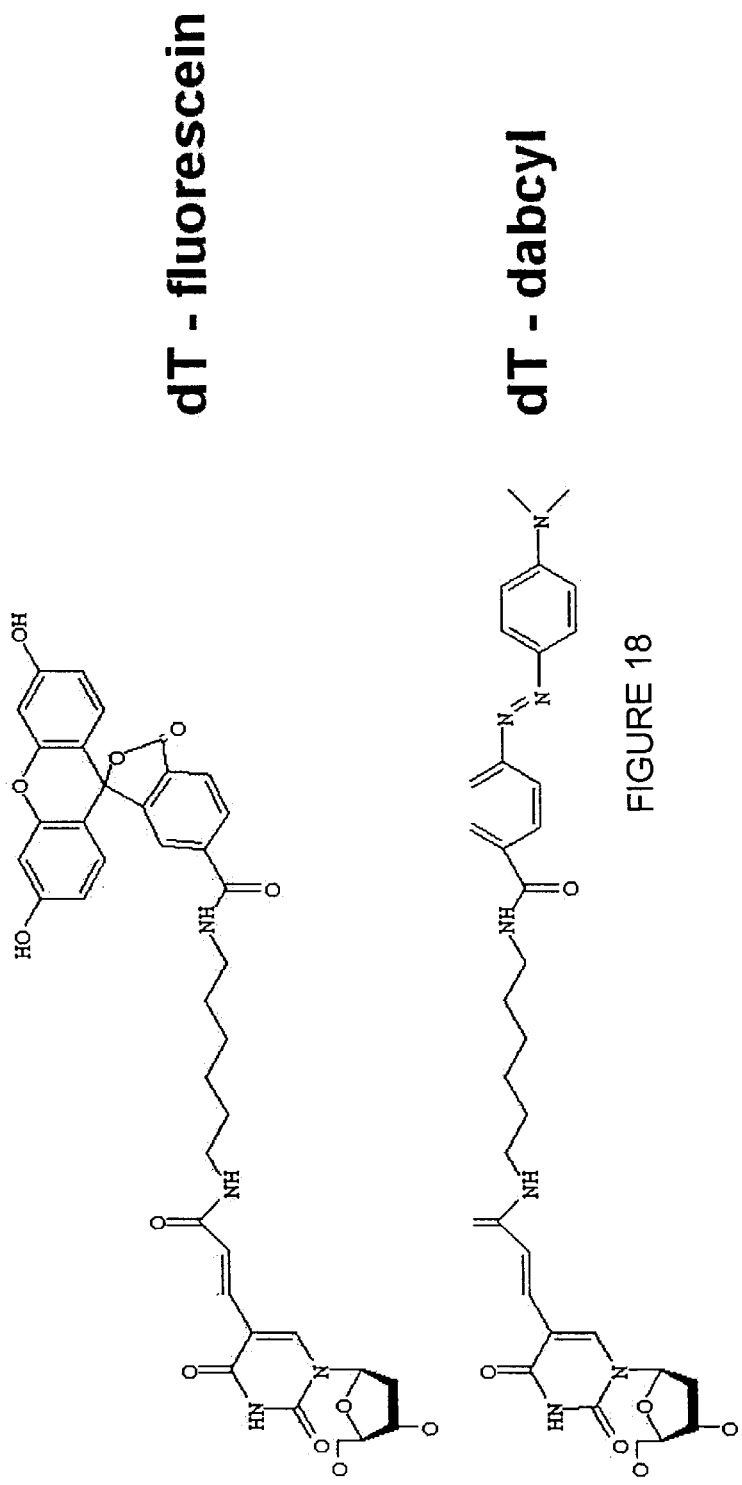
FIG. 18 depicts the nucleic acid duplexes of SEQ ID NO:20–23 containing portions of the p53 protein DNA binding element.

The oligonucleotides were purified using reverse phase chromatography on a RPC column as described previously (Heyduk, E., and Heyduk, supra). The fractions containing the oligonucleotides were dried in Vacuum centrifuge concentrator and were dissolved in 50 µl of water. The concentrations of the stock solutions of oligonucleotides were determined by recording the UV-VIS absorption spectrum of a small aliquot of the stock solution diluted to 400 µl. The P1 oligonucleotide (SEQ ID NO:20) was hybridized with the P4 oligonucleotide (SEQ ID NO:23) to generate the P1/P4 duplex construct and the P2 oligonucleotide (SEQ ID NO:21) was hybridized with the P3 (SEQ ID NO:22) oligonucleotide to generate the P2/P3 duplex construct. For the hybridization, the appropriate oligonucleotides were mixed at 10 µM concentration in 100 µl of 50 mM Tris/HCl (pH 8.0), 100 mM NaCl, 1 mM EDTA, heated for 1 min at 95° C. and then cooled to 25° C. for 1 hr. All subsequent fluorescence measurements were performed at 25° C. in 50-mM potassium phosphate (pH 7.5), 50 mM NaCl, and 0.5 mg/ml BSA containing also 100 nM of a nonspecific 30-bp DNA duplex. The DNA duplexes obtained upon hybridization are illustrated in FIG. 18. The duplexes contain a repeat of 10 bp PuPuPuC(A/T)(T/A)GPyPyPy (SEQ ID NO:24) motif split between the two DNA duplexes. This sequence (SEQ ID NO:24) has been identified as a consensus p53 recognition sequence (El-Deiry, W. S., Kern, S. E., Pietenpol, J. A., Kinzler, K. W., and Vogelstein, B. *Nature Genetics*, 1, 45–49, 1992). The p53 protein used in this assay was a human recombinant full-length protein expressed in bacteria (a gift from Dr. Kathleen S. Matthews; Nichols, N. M., and Matthews, K. S. *Biochemistry* 40, 3847–3858, 2001, which is herein incorporated by reference).

Figure 19:
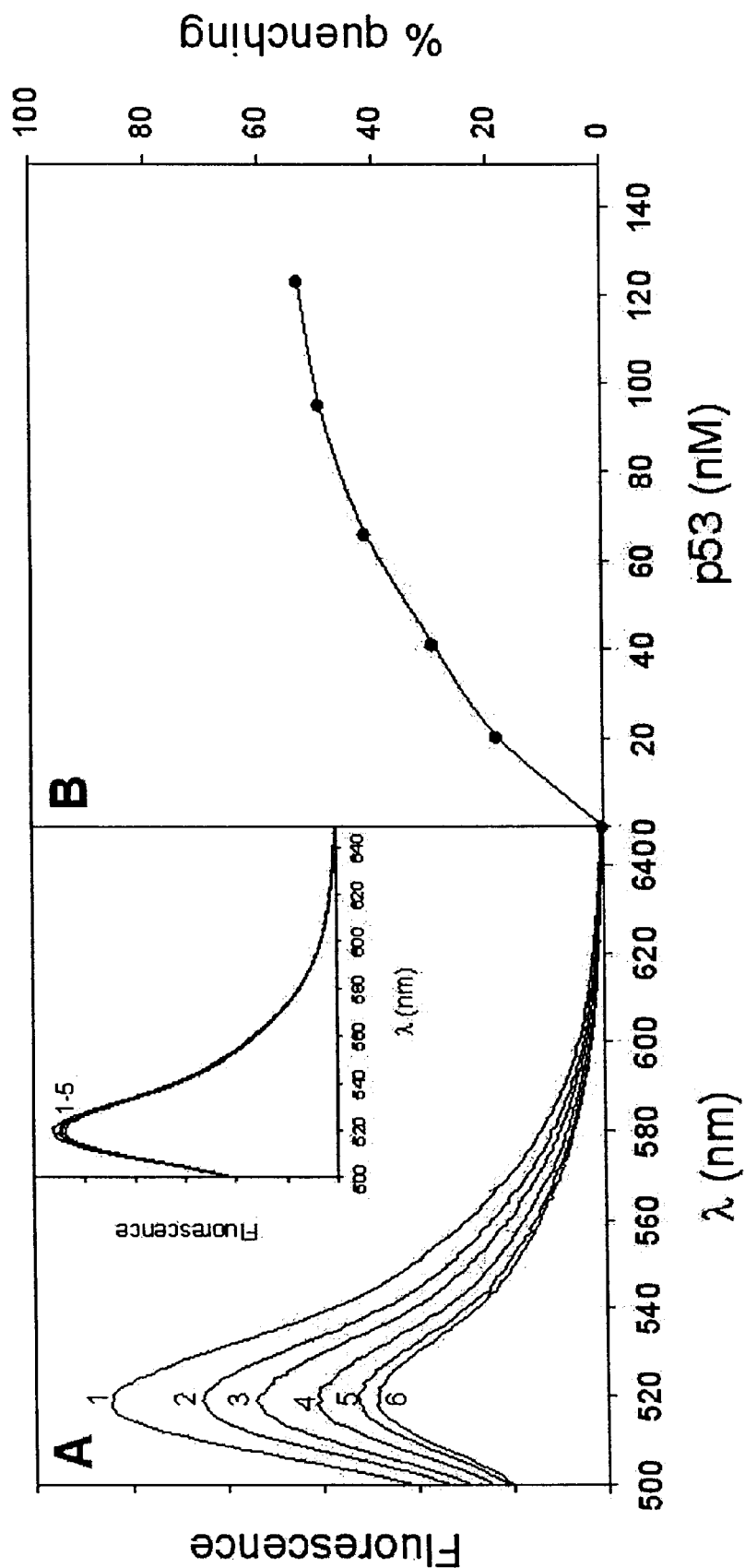
FIG. 19 depicts fluorescent quenching due to the binding of p53 protein to the cognate DNA binding element sequences. Curves 1–5 represent increasing amounts of p53 protein, from 0 to 130 nM, respectively.

The fluorescence spectra of 25 nM P1/P4 plus 30 nM P2/P3 were recorded in the absence of p53 protein (FIG. 19A, curve 1) and in the presence of varying amounts of p53 in a range from 0–130 nM (FIG. 19A, curves 2–6). The observed quenching of the fluorescence signal was proportional to the amount of p53 protein added to the assay mixture (FIG. 19B). The specificity of this particular assay for p53 detection was confirmed, by the demonstrating a lack of fluorescence quenching upon addition of p53 protein to a reaction mixture containing the nucleic acid constructs CAP1/CAP4 plus CAP2/CAP3 (FIG. 19A, inset, curve 1 corresponds to the signal in the absence of p53 whereas curves 4–5 correspond to the signal observed upon adding 1–90 nM p53). Taken together, this example demonstrates that the present invention is universally applicable to any and all DNA binding proteins, including important mammalian tumor suppressor proteins, e.g., p53.

As will be apparent to those skilled in the art in the light of the foregoing disclosures, many modifications, alterations and substitutions are possible in the practice of the present invention without departing from the spirit or scope thereof.

I claim:

1. A method of determining the activity of a DNA binding factor in a sample comprising combining two double stranded nucleic acid components with the sample wherein
   (a) each nucleic acid component comprises a portion of a DNA binding element wherein the combination of both nucleic acid components comprises a complete DNA binding element,
   (b) one nucleic acid component is labeled with a fluorescence donor and the other nucleic acid component is labeled with a fluorescence acceptor, and
   (c) the binding of a DNA binding factor or factors contained within the sample to the DNA binding element is detected by a proximity-based luminescence detection.

2. The method of claim 1 wherein
   (a) the DNA binding factor is selected from the group consisting of transcription factor, chromatin remodeling factor and genome maintenance enzyme, and
   (b) the proximity-based luminescence detection method is selected from the group consisting of fluorescence resonance energy transfer ("FRET"), luminescence resonance energy transfer ("LRET"), fluorescence cross-correlation spectroscopy ("FCCS"), flow cytometry, scintillation proximity ("SPA"), direct quenching, ground-state complex formation, chemiluminescence energy transfer ("CRET"), bioluminescence energy transfer ("BRET") and excimer formation.

3. The method of claim 2 wherein the DNA binding factor is a transcription factor.

4. The method of claim 2 wherein the proximity-based luminescence detection method is FRET.

5. The method of claim 4 wherein the two nucleic acid components are joined by a linker.

6. The method of claim 4 wherein the nucleic acid components are attached to a solid substrate.

7. The method of claim 2 wherein the two nucleic acid components are joined by a linker.

8. The method of claim 2 wherein the nucleic acid components are attached to a solid substrate.

9. The method of claim 3 wherein the two nucleic acid components are joined by a linker.

10. The method of claim 3 wherein the nucleic acid components are attached to a solid substrate.

11. The method of claim 1 wherein the two nucleic acid components are joined by a linker.

12. The method of claim 1 wherein the nucleic acid components are attached to a solid substrate.

13. A method of detecting enhanceosome proteins in a sample comprising combining a DNA molecule with said sample wherein
    (a) the DNA molecule comprises at least two DNA binding elements,
    (b) the DNA molecule is labeled at one position with a fluorescence donor and at another position with a fluorescence acceptor,
    (c) the binding of one or more enhanceosome proteins to the DNA molecule is detected by a proximity-based luminescence detection method.

14. The method of claim 13 wherein the linker is comprised of spacer 18 phosphoramidate moieties.

15. The method of claim 13 wherein the DNA molecule is attached to a solid substrate.

16. The method of claim 15 wherein the proximity-based luminescence detection method is selected from the group consisting of fluorescence resonance energy transfer ("FRET"), luminescence resonance energy transfer ("LRET"), fluorescence cross-correlation spectroscopy ("FCCS"), flow cytometry, scintillation proximity ("SPA"), direct quenching, ground-state complex formation, chemiluminescence energy transfer ("CRET"), bioluminescence energy transfer ("BRET") and excimer formation.

17. The method of claim 13 wherein the proximity-based luminescence detection method is selected from the group consisting of fluorescence resonance energy transfer ("FRET"), luminescence resonance energy transfer ("LRET"), fluorescence cross-correlation spectroscopy ("FCCS"), flow cytometry, scintillation proximity ("SPA"), direct quenching, ground-state complex formation, chemiluminescence energy transfer ("CRET"), bioluminescence energy transfer ("BRET") and excimer formation.

18. The method of claim 17 wherein the proximity-based luminescence detection method is FRET.

19. A method of detecting or quantifying the amount of an analyte in a sample comprising combining two double stranded nucleic acid components and at least one DNA binding factor with the sample wherein
    (a) each nucleic acid component comprises a portion of a DNA binding element wherein the combination of both nucleic acid components comprises a complete DNA binding element;
    (b) one nucleic acid component is labeled with a fluorescence donor and the other nucleic acid component is labeled with a fluorescence acceptor,
    (c) the association of the DNA binding factor to the DNA binding element is detected by a proximity-based luminescence detection method, wherein the association of the DNA binding factor to the DNA binding element is mediated by the analyte.

20. The method of claim 19 wherein
    (a) the DNA binding factor is selected from the group consisting of transcription factor, chromatin remodeling factor and genome maintenance enzyme,
    (b) the proximity-based luminescence detection method is selected from the group consisting of fluorescence resonance energy transfer ("FRET"), luminescence resonance energy transfer ("LRET"), fluorescence cross-correlation spectroscopy ("FCCS"), flow cytometry, scintillation proximity ("SPA"), direct quenching, ground-state complex formation, chemiluminescence energy transfer ("CRES"), bioluminescence energy transfer ("BRET") and excimer formation, and (c) the analyte is selected from the group consisting of secondary messenger molecule, drug, agent, reagent, prospective drug, prospective agent and prospective reagent.

21. The method of claim 20 wherein the DNA binding factor is a genome maintenance enzyme.

22. The method of claim 21 wherein the nucleic acid components are attached to a solid substrate.

23. The method of claim 21 wherein the nucleic acid components are attached to a soild substrate.

24. The method of claim 20 wherein the proximity-based luminescence detection method is FRET.

25. The method of claim 24 wherein the transcription factor is CAP and the analyte is cAMP.

26. The method of claim 25 wherein the two nucleic acid components are joined by a linker.

27. The method of claim 25 wherein the nucleic acid components are attached to a solid substrate.

28. The method of claim 24 wherein the two nucleic acid components are joined by a linker.

29. The method of claim 24 wherein the nucleic acid components are attached to a solid substrate.

30. The method of claim 20 wherein the two nucleic acid components are joined by a linker.

31. The method of claim 30 wherein the linker is comprised of spacer 18 phosphoramidate moieties.

32. The method of claim 20 wherein the nucleic acid components are attached to a solid substrate.

33. A method of detecting or quantifying the amount of multiple different DNA binding factors in a sample comprising combining at least two sets of double stranded nucleic acid components with the sample wherein (a) each nucleic acid component of a set of nucleic acid components comprises a portion of a DNA binding element wherein the combination of both nucleic acid components of a said set of nucleic acid components comprises a complete DNA binding element, (b) one nucleic acid component of a set of nucleic acid components is labeled with a fluorescence donor and the other nucleic acid component of a set of nucleic acid components is labeled with a fluorescence acceptor, (c) each set of nucleic acid components is labeled with a unique combination of fluorescent donor and acceptor which emits light at a unique wavelength, and (d) the binding of one or more DNA binding factors contained within the sample to the DNA binding element is detected by a proximity-based luminescence detection method.

34. The method of claim 33 wherein (a) the DNA binding factors are selected from the group consisting of transcription factor, chromatin remodeling factor and genome maintenance enzyme, and (b) the proximity-based luminescence detection method is selected from the group consisting of fluorescence resonance energy transfer ("FRET"), luminescence resonance energy transfer ("LRET"), fluorescence cross-correlation spectroscopy ("FCCS"), flow cytometry, scintillation proximity ("SPA"), direct quenching, ground-state complex formation, chemiluminescence energy transfer ("CRET"), bioluminescence energy transfer ("BRET") and excimer formation.

35. The method of claim 34 wherein the proximity-based luminescence detection method is FRET.

36. A method for diagnosing a disease mediated by a DNA binding factor comprising combining a sample obtained from a subject with at least two double stranded nucleic acid components wherein (a) each nucleic acid component comprises a portion of a DNA binding element wherein the combination of both nucleic acid components comprises a complete DNA binding element, (b) one nucleic acid component is labeled with a fluorescence donor and the other nucleic acid component is labeled with a fluorescence acceptor, (c) the sample comprises cellular extracts, and (d) the binding of a DNA binding factor or factors contained within the sample to the DNA binding element is detected by a proximity-based luminescence detection method.

37. The method of claim 36 wherein (a) the DNA binding factor is selected from the group consisting of transcription factor, chromatin remodeling factor and genome maintenance enzyme, and (b) the proximity-based luminescence detection method is selected from the group consisting of fluorescence resonance energy transfer ("FRET"), luminescence resonance energy transfer ("LRET"), fluorescence cross-correlation spectroscopy ("FCCS"), flow cytometry, scintillation proximity ("SPA"), direct quenching, ground-state complex formation, chemiluminescence energy transfer ("CRET"), bioluminescence energy transfer ("BRET") and excimer formation.

38. The method of claim 37 wherein the DNA binding factor is a genome maintenance enzyme.

39. The method of claim 38 wherein the genome maintenance enzyme is p53.

40. The method of claim 37 wherein the proximity-based luminescence detection method is FRET.

41. The method of claim 37 wherein the subject is a human patient.

42. The method of claim 37 wherein the human patient suffers from a type of cancer or disease of genome instability.

43. A method of determining the activity of a DNA binding factor in a sample comprising combining two double stranded nucleic acid components with the sample wherein (a) each nucleic acid component comprises a portion of a DNA binding element wherein the combination of both nucleic acid components comprises a complete DNA binding element, (b) one nucleic acid component is labeled with an enzyme, cofactor or catalyst and the other nucleic acid component Is labeled with a chemiluminescent substrate or a colorimetric substrate, and (c) the binding of a DNA binding factor or factors contained within the sample to the DNA binding element is determined by the detection of a change in luminescence or color.

44. A method of determining the activity of a DNA binding factor in a sample comprising combining two double stranded nucleic acid components with the sample wherein (a) each nucleic acid component comprises a portion of a DNA binding element wherein the combination of both nucleic acid components comprises a complete DNA binding element, (b) one nucleic acid component is linked to a microsphere and the other nucleic acid component is labeled with a flourochrome, and (c) the binding of a DNA binding factor or factors contained within the sample to the DNA binding element is determined by flow cytometry.

45. A method of determining the affinity of a DNA binding factor for a variant nucleic acid sequence comprising combining the varient nucleic acid sequence with the DNA binding factor and two double stranded nucleic acid components wherein (a) each nucleic acid component comprises a portion of a DNA binding element wherein the combination of both nucleic acid components comprises a complete DNA binding element, (b) one nucleic acid component is labeled with a fluorescence donor and the other nucleic acid component is labeled with a fluorescence.

46. A method of determining the activity of a DNA binding factor in a sample comprising combining two double stranded nucleic acid components with the sample wherein (a) each nucleic acid component comprises a portion of a DNA binding element wherein the combination of both nucleic acid components comprises a complete DNA binding element, (b) one nucleic acid component is linked to a microsphere that is imbued with a scintillant and the other nucleic acid component is labeled with a radioisotope, and (c) the binding of a DNA binding factor or factors contained within the sample to the DNA binding element is determined by a scintillation proximity assay.

* * * * *